US012746280B2

(12) United States Patent
Zhan et al.

(10) Patent No.: US 12,746,280 B2
(45) Date of Patent: Sep. 29, 2026

(54) CHAGAS DISEASE VACCINE ANTIGENS WITH IMPROVED STABILITY AND DECREASED AGGREGATION

(71) Applicant: Baylor College of Medicine, Houston, TX (US)

(72) Inventors: Bin Zhan, Houston, TX (US); Peter Jay Hotez, Houston, TX (US); Maria Elena Botazzi, Houston, TX (US); Jaime Ortega-Lopez, Cuidad de Mexico (MX)

(73) Assignee: Baylor College of Medicine, Houston, TX (US)

( * ) Notice: Subject to any disclaimer, the term of this patent is extended or adjusted under 35 U.S.C. 154(b) by 964 days.

(21) Appl. No.: 17/769,113

(22) PCT Filed: Oct. 14, 2020

(86) PCT No.: PCT/US2020/055504

§ 371 (c)(1),
(2) Date: Apr. 14, 2022

(87) PCT Pub. No.: WO2021/076570

PCT Pub. Date: Apr. 22, 2021

(65) Prior Publication Data

US 2024/0108707 A1 Apr. 4, 2024

Related U.S. Application Data

(60) Provisional application No. 62/916,391, filed on Oct. 17, 2019.

(51) Int. Cl.

| | |
|---|---|
| ***A61K 39/005*** | (2006.01) |
| ***A61K 31/519*** | (2006.01) |
| ***A61P 33/02*** | (2006.01) |

(52) U.S. Cl.

CPC .......... *A61K 39/005* (2013.01); *A61K 31/519* (2013.01); *A61P 33/02* (2018.01)

(58) Field of Classification Search

None

See application file for complete search history.

(56) References Cited

FOREIGN PATENT DOCUMENTS

| | | |
|---|---|---|
| WO | 2004067040 A1 | 8/2004 |
| WO | 2017160849 A1 | 9/2017 |

OTHER PUBLICATIONS

Prengler et al, Ann Neurol 2002;51:543-552. (Year: 2002).*
Witkowski et al, Biochemistry 38:11643-11650, 1999. (Year: 1999).*
Seffernick et al, Bacteriol. 183(8): 2405-2410, 2001. (Year: 2001).*

* cited by examiner

*Primary Examiner* — Misook Yu
*Assistant Examiner* — Cheom-Gil Cheong
(74) *Attorney, Agent, or Firm* — WCF IP

(57) ABSTRACT

Provided herein are compositions and methods for the prevention and treatment of Chagas disease and acute and chronic symptoms thereof. The compositions comprise recombinant proteins based on an amino terminal fragment of the TSA-1 protein from *Trypanosoma cruzi*. In the fragment, one or more Cys residues is mutated to prevent the formation of disulfide bonds and to enhance solubility. The recombinant proteins also include a carboxyl terminal fragment of the TSA-1 protein from *Trypanosoma cruzi* to provide additional stability and solubility. The resulting recombinant protein remains soluble upon prolonged storage at low temperatures and elicits a robust immune response upon administration, including decreasing the number of inflammatory cells in heart tissue of subjects.

14 Claims, 12 Drawing Sheets

Specification includes a Sequence Listing.

```
MERNSGDLQL PQEIAMLVPN KTQVVPKSGG EGKVKDIFAS PALVRAGGVM IAFVEGRTKN    60
KLFPEVIDLS SSDIVAGYIK APETWQSLVA EVTKEYWQAH TVLESANNSN HRVGVARLPT   120
GITRGNKVFL LVGSYEERRE IDDYIWKAEA WNIKVIEGEA TQSTEVQPTQ PINWSEPKPL   180
FQTDSPNNKG DLKEFLGGGG SGIVMGNGTL VFPLTAKDES NKVFSLITYS TDDGQKWEIP   240
GGVSSVAX1RS PRVTEWEEGT LLMVTYX2EDG RKVFESRDMG KTWTEAFGTL PGVWLKSGPE   300
LPEVSLRVDA LITATIEGRK VMLYTQKVRH FLEVDEPNAL HLWVTDNNRT FHLGPFSVDX3  360
AENKTFANTL LYSDDALHLL QAKGDHESTA VSLARLTEEL NTINSVLSTW VQLDASFSES   420
SIPTAGLVGF LSNTTSSGDT WIDGYRX4MNA TVTKAAKVEN GFKFTGPGSR ATWPVNSRWD  480
IKQYGFVDYN FTIVAMATIH QVPSESTPLL GASLRGNKRT KLIGLSYGAG GKWETVYDGT   540
KTVQGGTWEP GREYQVALML QDGNKGFVYV DGVLVGNPAM LPTPEERWTE FSHFYFGGDE   600
GDSGSDATLT DVFLYNRPLS VGELKMIKEV ED                                 632
```

(SEQ ID NO: 1)

Figure 1

```
TSA1-NT     1 MERNS GDLQL PQEIA MLVPN KTQVV PKSGG EGKVK DIFAS PALVR AGGVM IAFVE GRTKN
TSA1-C4     1 MERNS GDLQL PQEIA MLVPN KTQVV PKSGG EGKVK DIFAS PALVR AGGVM IAFVE GRTKN

TSA1-NT    61 KLFPE VIDLS SSDIV AGYIK APETW QSLVA EVTKE YWQAH TVLES ANNSN HRVGV ARLPT
TSA1-C4    61 KLFPE VIDLS SSDIV AGYIK APETW QSLVA EVTKE YWQAH TVLES ANNSN HRVGV ARLPT

TSA1-NT   121 GITRG NKVFL LVGSY EERRE IDDYI WKAEA WNIKV IEGEA TQSTE VQPTQ PINWS EPKPL
TSA1-C4   121 GITRG NKVFL LVGSY EERRE IDDYI WKAEA WNIKV IEGEA TQSTE VQPTQ PINWS EPKPL

TSA1-NT   181 FQTDS PNNKG DLKEF LGGGG SGIVM GNGTL VFPLT AKDES NKVFS LITYS TDDGQ KWEIP
TSA1-C4   181 FQTDS PNNKG DLKEF LGGGG SGIVM GNGTL VFPLT AKDES NKVFS LITYS TDDGQ KWEIP

TSA1-NT   241 GGVSS VACRS PRVTE WEEGT LLMVT YCEDG RKVFE SRDMG KTWTE AFGTL PGVWL KSGPE
TSA1-C4   241 GGVSS VASRS PRVTE WEEGT LLMVT YSEDG RKVFE SRDMG KTWTE AFGTL PGVWL KSGPE

TSA1-NT   301 LPEVS LRVDA LITAT IEGRK VMLYT QKVRH FLEVD EPNAL HLWVT DNNRT FHLGP FSVDC
TSA1-C4   301 LPEVS LRVDA LITAT IEGRK VMLYT QKVRH FLEVD EPNAL HLWVT DNNRT FHLGP FSVDS

TSA1-NT   361 AENKT FANTL LYSDD ALHLL QAKGD HESTA VSLAR LTEEL NTINS VLSTW VQLDA SFSES
TSA1-C4   361 AENKT FANTL LYSDD ALHLL QAKGD HESTA VSLAR LTEEL NTINS VLSTW VQLDA SFSES

TSA1-NT   421 SIPTA GLVGF LSNTT SSGDT WIDGY RCMNA TVTKA AKVEN GFKFT GPGSR ATWPV NSRWD
TSA1-C4   421 SIPTA GLVGF LSNTT SSGDT WIDGY RSMNA TVTKA AKVEN GFKFT GPGSR ATWPV NSRWD

TSA1      481 IKQYG FVDYN FTIVA MATIH QVPSE STPLL GASLR GNKRT KLIGL SYGAG GKWET VYDGT
TSA1-C4   481 IKQYG FVDYN FTIVA MATIH QVPSE STPLL GASLR GNKRT KLIGL SYGAG GKWET VYDGT

TSA1-NT   541 KTVQG GTWEP GREYQ VALML QDGNK GFVYV DGVLV GNPAM LPTPE ERWT------------
TSA1-C4   541 KTVQG GTWEP GREYQ VALML QDGNK GFVYV DGVLV GNPAM LPTPE ERWTE FSHFY FGGDE

TSA1-NT       -------------------------------------            (SEQ ID NO: 2)
TSA1-C4   601 GDSGS DATLT DVFLY NRPLS VGELK MIKEV ED               (SEQ ID NO: 3)
```

Figure 2

MERNSGDLQLPQEIAMLVPNKTQVVPKSGGEGKVKDIFASPALVRAGGVMIAF
VEGRTKNKLFPEVIDLSSSDIVAGYIKAPETWQSLVAEVTKEYWQAHTVLESA
NNSNHRVGVARLPTGITRGNKVFLLVGSYEERREIDDYIWKAEAWNIKVIEGE
ATQSTEVQPTQPINWSEPKPLFQTDSPNNKGDLKEFLGGGGSGIVMGNGTLVF
PLTAKDESNKVFSLITYSTDDGQKWEIPGGVSSVASRSPRVTEWEEGTLLMVT
YSEDGRKVFESRDMGKTWTEAFGTLPGVWLKSGPELPEVSLRVDALITATIEG
RKVMLYTQKVRHFLEVDEPNALHLWVTDNNRTFHLGPFSVDSAENKTFANTLL
YSDDALHLLQAKGDHESTAVSLARLTEELNTINSVLSTWVQLDASFSESSIPT
AGLVGFLSNTTSSGDTWIDGYRSMNATVTKAAKVENGFKFTGPGSRATWPVNS
RWDIKQYGFVDYNFTIVAMATIHQVPSESTPLLGASLRGNKRTKLIGLSYGAG
GKWETVYDGTKTVQGGTWEPGREYQVALMLQDGNKGFVYVDGVLVGNPAMLPT
PEERWTEFSHFYFGGDEGDSGSDATLTDVFLYNRPLSVGELKMIKEVEDLEHH
HHHHHH (SEQ ID NO: 4)

Figure 5A

MERNSGDLQLPQEIAMLVPNKTQVVPKSGGEGKVKDIFASPALVRAGGVMIAF
VEGRTKNKLFPEVIDLSSSDIVAGYIKAPETWQSLVAEVTKEYWQAHTVLESA
NNSNHRVGVARLPTGITRGNKVFLLVGSYEERREIDDYIWKAEAWNIKVIEGE
ATQSTEVQPTQPINWSEPKPLFQTDSPNNKGDLKEFLGGGGSGIVMGNGTLVF
PLTAKDESNKVFSLITYSTDDGQKWEIPGGVSSVASRSPRVTEWEEGTLLMVT
YSEDGRKVFESRDMGKTWTEAFGTLPGVWLKSGPELPEVSLRVDALITATIEG
RKVMLYTQKVRHFLEVDEPNALHLWVTDNNRTFHLGPFSVDSAENKTFANTLL
YSDDALHLLQAKGDHESTAVSLARLTEELNTINSVLSTWVQLDASFSESSIPT
AGLVGFLSNTTSSGDTWIDGYRSMNATVTKAAKVENGFKFTGPGSRATWPVNS
RWDIKQYGFVDYNFTIVAMATIHQVPSESTPLLGASLRGNKRTKLIGLSYGAG
GKWETVYDGTKTVQGGTWEPGREYQVALMLQDGNKGFVYVDGVLVGNPAMLPT
PEERWTEFSHFYFGGDEGDSGSDATLTDVFLYNRPLSVGELKMIKEVED
(SEQ ID NO: 3)

Figure 5B

TSA-1-C4-His/pET41a/BL1

SEQUENCE LISTING

<160> NUMBER OF SEQ ID NOS: 11

<210> SEQ ID NO 1
<211> LENGTH: 632
<212> TYPE: PRT
<213> ORGANISM: Artificial Sequence
<220> FEATURE:
<223> OTHER INFORMATION: generic synthetic recombinant protein based on residues 30-660 of TSA1 from T. cruzi
<220> FEATURE:
<221> NAME/KEY: MISC_FEATURE
<222> LOCATION: (248)..(248)
<223> OTHER INFORMATION: Xaa can be any naturally occurring amino acid
<220> FEATURE:
<221> NAME/KEY: MISC_FEATURE
<222> LOCATION: (267)..(267)
<223> OTHER INFORMATION: Xaa can be any naturally occurring amino acid
<220> FEATURE:
<221> NAME/KEY: MISC_FEATURE
<222> LOCATION: (360)..(360)
<223> OTHER INFORMATION: Xaa can be any naturally occurring amino acid
<220> FEATURE:
<221> NAME/KEY: MISC_FEATURE
<222> LOCATION: (447)..(447)
<223> OTHER INFORMATION: Xaa can be any naturally occurring amino acid

<400> SEQUENCE: 1

```
Met Glu Arg Asn Ser Gly Asp Leu Gln Leu Pro Gln Glu Ile Ala Met
1               5                   10                  15

Leu Val Pro Asn Lys Thr Gln Val Val Pro Lys Ser Gly Gly Glu Gly
            20                  25                  30

Lys Val Lys Asp Ile Phe Ala Ser Pro Ala Leu Val Arg Ala Gly Gly
        35                  40                  45

Val Met Ile Ala Phe Val Glu Gly Arg Thr Lys Asn Lys Leu Phe Pro
    50                  55                  60

Glu Val Ile Asp Leu Ser Ser Ser Asp Ile Val Ala Gly Tyr Ile Lys
65                  70                  75                  80

Ala Pro Glu Thr Trp Gln Ser Leu Val Ala Glu Val Thr Lys Glu Tyr
                85                  90                  95

Trp Gln Ala His Thr Val Leu Glu Ser Ala Asn Asn Ser Asn His Arg
            100                 105                 110

Val Gly Val Ala Arg Leu Pro Thr Gly Ile Thr Arg Gly Asn Lys Val
        115                 120                 125

Phe Leu Leu Val Gly Ser Tyr Glu Glu Arg Arg Glu Ile Asp Asp Tyr
    130                 135                 140

Ile Trp Lys Ala Glu Ala Trp Asn Ile Lys Val Ile Glu Gly Glu Ala
145                 150                 155                 160

Thr Gln Ser Thr Glu Val Gln Pro Thr Gln Pro Ile Asn Trp Ser Glu
                165                 170                 175

Pro Lys Pro Leu Phe Gln Thr Asp Ser Pro Asn Asn Lys Gly Asp Leu
            180                 185                 190

Lys Glu Phe Leu Gly Gly Gly Gly Ser Gly Ile Val Met Gly Asn Gly
        195                 200                 205

Thr Leu Val Phe Pro Leu Thr Ala Lys Asp Glu Ser Asn Lys Val Phe
    210                 215                 220

Ser Leu Ile Thr Tyr Ser Thr Asp Asp Gly Gln Lys Trp Glu Ile Pro
225                 230                 235                 240

Gly Gly Val Ser Ser Val Ala Xaa Arg Ser Pro Arg Val Thr Glu Trp
                245                 250                 255

Glu Glu Gly Thr Leu Leu Met Val Thr Tyr Xaa Glu Asp Gly Arg Lys
            260                 265                 270
```

```
Val Phe Glu Ser Arg Asp Met Gly Lys Thr Trp Thr Glu Ala Phe Gly
        275                 280                 285

Thr Leu Pro Gly Val Trp Leu Lys Ser Gly Pro Glu Leu Pro Glu Val
    290                 295                 300

Ser Leu Arg Val Asp Ala Leu Ile Thr Ala Thr Ile Glu Gly Arg Lys
305                 310                 315                 320

Val Met Leu Tyr Thr Gln Lys Val Arg His Phe Leu Glu Val Asp Glu
                325                 330                 335

Pro Asn Ala Leu His Leu Trp Val Thr Asp Asn Asn Arg Thr Phe His
            340                 345                 350

Leu Gly Pro Phe Ser Val Asp Xaa Ala Glu Asn Lys Thr Phe Ala Asn
        355                 360                 365

Thr Leu Leu Tyr Ser Asp Asp Ala Leu His Leu Leu Gln Ala Lys Gly
    370                 375                 380

Asp His Glu Ser Thr Ala Val Ser Leu Ala Arg Leu Thr Glu Glu Leu
385                 390                 395                 400

Asn Thr Ile Asn Ser Val Leu Ser Thr Trp Val Gln Leu Asp Ala Ser
                405                 410                 415

Phe Ser Glu Ser Ser Ile Pro Thr Ala Gly Leu Val Gly Phe Leu Ser
            420                 425                 430

Asn Thr Thr Ser Ser Gly Asp Thr Trp Ile Asp Gly Tyr Arg Xaa Met
        435                 440                 445

Asn Ala Thr Val Thr Lys Ala Ala Lys Val Glu Asn Gly Phe Lys Phe
    450                 455                 460

Thr Gly Pro Gly Ser Arg Ala Thr Trp Pro Val Asn Ser Arg Trp Asp
465                 470                 475                 480

Ile Lys Gln Tyr Gly Phe Val Asp Tyr Asn Phe Thr Ile Val Ala Met
                485                 490                 495

Ala Thr Ile His Gln Val Pro Ser Glu Ser Thr Pro Leu Leu Gly Ala
            500                 505                 510

Ser Leu Arg Gly Asn Lys Arg Thr Lys Leu Ile Gly Leu Ser Tyr Gly
        515                 520                 525

Ala Gly Gly Lys Trp Glu Thr Val Tyr Asp Gly Thr Lys Thr Val Gln
    530                 535                 540

Gly Gly Thr Trp Glu Pro Gly Arg Glu Tyr Gln Val Ala Leu Met Leu
545                 550                 555                 560

Gln Asp Gly Asn Lys Gly Phe Val Tyr Val Asp Gly Val Leu Val Gly
                565                 570                 575

Asn Pro Ala Met Leu Pro Thr Pro Glu Glu Arg Trp Thr Glu Phe Ser
            580                 585                 590

His Phe Tyr Phe Gly Gly Asp Glu Gly Asp Ser Gly Ser Asp Ala Thr
        595                 600                 605

Leu Thr Asp Val Phe Leu Tyr Asn Arg Pro Leu Ser Val Gly Glu Leu
    610                 615                 620

Lys Met Ile Lys Glu Val Glu Asp
625                 630
```

```
<210> SEQ ID NO 2
<211> LENGTH: 631
<212> TYPE: PRT
<213> ORGANISM: Artificial Sequence
<220> FEATURE:
<223> OTHER INFORMATION: synthetic recombinant protein based on residues
      30-660 of TSA1 from T. cruzi
```

<400> SEQUENCE: 2

```
Glu Arg Asn Ser Gly Asp Leu Gln Leu Pro Gln Glu Ile Ala Met Leu
1               5                   10                  15

Val Pro Asn Lys Thr Gln Val Val Pro Lys Ser Gly Gly Glu Gly Lys
            20                  25                  30

Val Lys Asp Ile Phe Ala Ser Pro Ala Leu Val Arg Ala Gly Gly Val
        35                  40                  45

Met Ile Ala Phe Val Glu Gly Arg Thr Lys Asn Lys Leu Phe Pro Glu
    50                  55                  60

Val Ile Asp Leu Ser Ser Ser Asp Ile Val Ala Gly Tyr Ile Lys Ala
65                  70                  75                  80

Pro Glu Thr Trp Gln Ser Leu Val Ala Glu Val Thr Lys Glu Tyr Trp
                85                  90                  95

Gln Ala His Thr Val Leu Glu Ser Ala Asn Asn Ser Asn His Arg Val
            100                 105                 110

Gly Val Ala Arg Leu Pro Thr Gly Ile Thr Arg Gly Asn Lys Val Phe
        115                 120                 125

Leu Leu Val Gly Ser Tyr Glu Glu Arg Arg Glu Ile Asp Asp Tyr Ile
    130                 135                 140

Trp Lys Ala Glu Ala Trp Asn Ile Lys Val Ile Glu Gly Glu Ala Thr
145                 150                 155                 160

Gln Ser Thr Glu Val Gln Pro Thr Gln Pro Ile Asn Trp Ser Glu Pro
                165                 170                 175

Lys Pro Leu Phe Gln Thr Asp Ser Pro Asn Asn Lys Gly Asp Leu Lys
            180                 185                 190

Glu Phe Leu Gly Gly Gly Gly Ser Gly Ile Val Met Gly Asn Gly Thr
        195                 200                 205

Leu Val Phe Pro Leu Thr Ala Lys Asp Glu Ser Asn Lys Val Phe Ser
    210                 215                 220

Leu Ile Thr Tyr Ser Thr Asp Asp Gly Gln Lys Trp Glu Ile Pro Gly
225                 230                 235                 240

Gly Val Ser Ser Val Ala Cys Arg Ser Pro Arg Val Thr Glu Trp Glu
                245                 250                 255

Glu Gly Thr Leu Leu Met Val Thr Tyr Cys Glu Asp Gly Arg Lys Val
            260                 265                 270

Phe Glu Ser Arg Asp Met Gly Lys Thr Trp Thr Glu Ala Phe Gly Thr
        275                 280                 285

Leu Pro Gly Val Trp Leu Lys Ser Gly Pro Glu Leu Pro Glu Val Ser
    290                 295                 300

Leu Arg Val Asp Ala Leu Ile Thr Ala Thr Ile Glu Gly Arg Lys Val
305                 310                 315                 320

Met Leu Tyr Thr Gln Lys Val Arg His Phe Leu Glu Val Asp Glu Pro
                325                 330                 335

Asn Ala Leu His Leu Trp Val Thr Asp Asn Asn Arg Thr Phe His Leu
            340                 345                 350

Gly Pro Phe Ser Val Asp Cys Ala Glu Asn Lys Thr Phe Ala Asn Thr
        355                 360                 365

Leu Leu Tyr Ser Asp Asp Ala Leu His Leu Leu Gln Ala Lys Gly Asp
    370                 375                 380

His Glu Ser Thr Ala Val Ser Leu Ala Arg Leu Thr Glu Glu Leu Asn
385                 390                 395                 400

Thr Ile Asn Ser Val Leu Ser Thr Trp Val Gln Leu Asp Ala Ser Phe
                405                 410                 415
```

```
Ser Glu Ser Ser Ile Pro Thr Ala Gly Leu Val Gly Phe Leu Ser Asn
            420                 425                 430

Thr Thr Ser Ser Gly Asp Thr Trp Ile Asp Gly Tyr Arg Cys Met Asn
        435                 440                 445

Ala Thr Val Thr Lys Ala Ala Lys Val Glu Asn Gly Phe Lys Phe Thr
    450                 455                 460

Gly Pro Gly Ser Arg Ala Thr Trp Pro Val Asn Ser Arg Trp Asp Ile
465                 470                 475                 480

Lys Gln Tyr Gly Phe Val Asp Tyr Asn Phe Thr Ile Val Ala Met Ala
                485                 490                 495

Thr Ile His Gln Val Pro Ser Glu Ser Thr Pro Leu Leu Gly Ala Ser
            500                 505                 510

Leu Arg Gly Asn Lys Arg Thr Lys Leu Ile Gly Leu Ser Tyr Gly Ala
        515                 520                 525

Gly Gly Lys Trp Glu Thr Val Tyr Asp Gly Thr Lys Thr Val Gln Gly
    530                 535                 540

Gly Thr Trp Glu Pro Gly Arg Glu Tyr Gln Val Ala Leu Met Leu Gln
545                 550                 555                 560

Asp Gly Asn Lys Gly Phe Val Tyr Val Asp Gly Val Leu Val Gly Asn
                565                 570                 575

Pro Ala Met Leu Pro Thr Pro Glu Glu Arg Trp Thr Glu Phe Ser His
            580                 585                 590

Phe Tyr Phe Gly Gly Asp Glu Gly Asp Ser Gly Ser Asp Ala Thr Leu
        595                 600                 605

Thr Asp Val Phe Leu Tyr Asn Arg Pro Leu Ser Val Gly Glu Leu Lys
    610                 615                 620

Met Ile Lys Glu Val Glu Asp
625                 630


<210> SEQ ID NO 3
<211> LENGTH: 632
<212> TYPE: PRT
<213> ORGANISM: Artificial Sequence
<220> FEATURE:
<223> OTHER INFORMATION: synthetic recombinant protein based on TSA1
      from T. cruzi

<400> SEQUENCE: 3

Met Glu Arg Asn Ser Gly Asp Leu Gln Leu Pro Gln Glu Ile Ala Met
1               5                   10                  15

Leu Val Pro Asn Lys Thr Gln Val Val Pro Lys Ser Gly Gly Glu Gly
            20                  25                  30

Lys Val Lys Asp Ile Phe Ala Ser Pro Ala Leu Val Arg Ala Gly Gly
        35                  40                  45

Val Met Ile Ala Phe Val Glu Gly Arg Thr Lys Asn Lys Leu Phe Pro
    50                  55                  60

Glu Val Ile Asp Leu Ser Ser Ser Asp Ile Val Ala Gly Tyr Ile Lys
65                  70                  75                  80

Ala Pro Glu Thr Trp Gln Ser Leu Val Ala Glu Val Thr Lys Glu Tyr
                85                  90                  95

Trp Gln Ala His Thr Val Leu Glu Ser Ala Asn Asn Ser Asn His Arg
            100                 105                 110

Val Gly Val Ala Arg Leu Pro Thr Gly Ile Thr Arg Gly Asn Lys Val
        115                 120                 125

Phe Leu Leu Val Gly Ser Tyr Glu Glu Arg Arg Glu Ile Asp Asp Tyr
```

-continued

```
    130                 135                 140

Ile Trp Lys Ala Glu Ala Trp Asn Ile Lys Val Ile Glu Gly Glu Ala
145                 150                 155                 160

Thr Gln Ser Thr Glu Val Gln Pro Thr Gln Pro Ile Asn Trp Ser Glu
                165                 170                 175

Pro Lys Pro Leu Phe Gln Thr Asp Ser Pro Asn Asn Lys Gly Asp Leu
            180                 185                 190

Lys Glu Phe Leu Gly Gly Gly Gly Ser Gly Ile Val Met Gly Asn Gly
        195                 200                 205

Thr Leu Val Phe Pro Leu Thr Ala Lys Asp Glu Ser Asn Lys Val Phe
    210                 215                 220

Ser Leu Ile Thr Tyr Ser Thr Asp Asp Gly Gln Lys Trp Glu Ile Pro
225                 230                 235                 240

Gly Gly Val Ser Ser Val Ala Ser Arg Ser Pro Arg Val Thr Glu Trp
                245                 250                 255

Glu Glu Gly Thr Leu Leu Met Val Thr Tyr Ser Glu Asp Gly Arg Lys
            260                 265                 270

Val Phe Glu Ser Arg Asp Met Gly Lys Thr Trp Thr Glu Ala Phe Gly
        275                 280                 285

Thr Leu Pro Gly Val Trp Leu Lys Ser Gly Pro Glu Leu Pro Glu Val
    290                 295                 300

Ser Leu Arg Val Asp Ala Leu Ile Thr Ala Thr Ile Glu Gly Arg Lys
305                 310                 315                 320

Val Met Leu Tyr Thr Gln Lys Val Arg His Phe Leu Glu Val Asp Glu
                325                 330                 335

Pro Asn Ala Leu His Leu Trp Val Thr Asp Asn Asn Arg Thr Phe His
            340                 345                 350

Leu Gly Pro Phe Ser Val Asp Ser Ala Glu Asn Lys Thr Phe Ala Asn
        355                 360                 365

Thr Leu Leu Tyr Ser Asp Asp Ala Leu His Leu Leu Gln Ala Lys Gly
    370                 375                 380

Asp His Glu Ser Thr Ala Val Ser Leu Ala Arg Leu Thr Glu Glu Leu
385                 390                 395                 400

Asn Thr Ile Asn Ser Val Leu Ser Thr Trp Val Gln Leu Asp Ala Ser
                405                 410                 415

Phe Ser Glu Ser Ser Ile Pro Thr Ala Gly Leu Val Gly Phe Leu Ser
            420                 425                 430

Asn Thr Thr Ser Ser Gly Asp Thr Trp Ile Asp Gly Tyr Arg Ser Met
        435                 440                 445

Asn Ala Thr Val Thr Lys Ala Ala Lys Val Glu Asn Gly Phe Lys Phe
    450                 455                 460

Thr Gly Pro Gly Ser Arg Ala Thr Trp Pro Val Asn Ser Arg Trp Asp
465                 470                 475                 480

Ile Lys Gln Tyr Gly Phe Val Asp Tyr Asn Phe Thr Ile Val Ala Met
                485                 490                 495

Ala Thr Ile His Gln Val Pro Ser Glu Ser Thr Pro Leu Leu Gly Ala
            500                 505                 510

Ser Leu Arg Gly Asn Lys Arg Thr Lys Leu Ile Gly Leu Ser Tyr Gly
        515                 520                 525

Ala Gly Gly Lys Trp Glu Thr Val Tyr Asp Gly Thr Lys Thr Val Gln
    530                 535                 540

Gly Gly Thr Trp Glu Pro Gly Arg Glu Tyr Gln Val Ala Leu Met Leu
545                 550                 555                 560
```

Gln Asp Gly Asn Lys Gly Phe Val Tyr Val Asp Gly Val Leu Val Gly
565 570 575

Asn Pro Ala Met Leu Pro Thr Pro Glu Glu Arg Trp Thr Glu Phe Ser
580 585 590

His Phe Tyr Phe Gly Gly Asp Glu Gly Asp Ser Gly Ser Asp Ala Thr
595 600 605

Leu Thr Asp Val Phe Leu Tyr Asn Arg Pro Leu Ser Val Gly Glu Leu
610 615 620

Lys Met Ile Lys Glu Val Glu Asp
625 630

<210> SEQ ID NO 4
<211> LENGTH: 642
<212> TYPE: PRT
<213> ORGANISM: Artificial Sequence
<220> FEATURE:
<223> OTHER INFORMATION: synthetic recombinant protein based on TSA1
from T. cruzi

<400> SEQUENCE: 4

Met Glu Arg Asn Ser Gly Asp Leu Gln Leu Pro Gln Glu Ile Ala Met
1 5 10 15

Leu Val Pro Asn Lys Thr Gln Val Val Pro Lys Ser Gly Gly Glu Gly
20 25 30

Lys Val Lys Asp Ile Phe Ala Ser Pro Ala Leu Val Arg Ala Gly Gly
35 40 45

Val Met Ile Ala Phe Val Glu Gly Arg Thr Lys Asn Lys Leu Phe Pro
50 55 60

Glu Val Ile Asp Leu Ser Ser Ser Asp Ile Val Ala Gly Tyr Ile Lys
65 70 75 80

Ala Pro Glu Thr Trp Gln Ser Leu Val Ala Glu Val Thr Lys Glu Tyr
85 90 95

Trp Gln Ala His Thr Val Leu Glu Ser Ala Asn Asn Ser Asn His Arg
100 105 110

Val Gly Val Ala Arg Leu Pro Thr Gly Ile Thr Arg Gly Asn Lys Val
115 120 125

Phe Leu Leu Val Gly Ser Tyr Glu Glu Arg Arg Glu Ile Asp Asp Tyr
130 135 140

Ile Trp Lys Ala Glu Ala Trp Asn Ile Lys Val Ile Glu Gly Glu Ala
145 150 155 160

Thr Gln Ser Thr Glu Val Gln Pro Thr Gln Pro Ile Asn Trp Ser Glu
165 170 175

Pro Lys Pro Leu Phe Gln Thr Asp Ser Pro Asn Asn Lys Gly Asp Leu
180 185 190

Lys Glu Phe Leu Gly Gly Gly Gly Ser Gly Ile Val Met Gly Asn Gly
195 200 205

Thr Leu Val Phe Pro Leu Thr Ala Lys Asp Glu Ser Asn Lys Val Phe
210 215 220

Ser Leu Ile Thr Tyr Ser Thr Asp Asp Gly Gln Lys Trp Glu Ile Pro
225 230 235 240

Gly Gly Val Ser Ser Val Ala Ser Arg Ser Pro Arg Val Thr Glu Trp
245 250 255

Glu Glu Gly Thr Leu Leu Met Val Thr Tyr Ser Glu Asp Gly Arg Lys
260 265 270

Val Phe Glu Ser Arg Asp Met Gly Lys Thr Trp Thr Glu Ala Phe Gly

-continued

```
        275                 280                 285

Thr Leu Pro Gly Val Trp Leu Lys Ser Gly Pro Glu Leu Pro Glu Val
    290                 295                 300

Ser Leu Arg Val Asp Ala Leu Ile Thr Ala Thr Ile Glu Gly Arg Lys
305                 310                 315                 320

Val Met Leu Tyr Thr Gln Lys Val Arg His Phe Leu Glu Val Asp Glu
                325                 330                 335

Pro Asn Ala Leu His Leu Trp Val Thr Asp Asn Asn Arg Thr Phe His
            340                 345                 350

Leu Gly Pro Phe Ser Val Asp Ser Ala Glu Asn Lys Thr Phe Ala Asn
        355                 360                 365

Thr Leu Leu Tyr Ser Asp Asp Ala Leu His Leu Leu Gln Ala Lys Gly
    370                 375                 380

Asp His Glu Ser Thr Ala Val Ser Leu Ala Arg Leu Thr Glu Glu Leu
385                 390                 395                 400

Asn Thr Ile Asn Ser Val Leu Ser Thr Trp Val Gln Leu Asp Ala Ser
                405                 410                 415

Phe Ser Glu Ser Ser Ile Pro Thr Ala Gly Leu Val Gly Phe Leu Ser
            420                 425                 430

Asn Thr Thr Ser Ser Gly Asp Thr Trp Ile Asp Gly Tyr Arg Ser Met
        435                 440                 445

Asn Ala Thr Val Thr Lys Ala Ala Lys Val Glu Asn Gly Phe Lys Phe
    450                 455                 460

Thr Gly Pro Gly Ser Arg Ala Thr Trp Pro Val Asn Ser Arg Trp Asp
465                 470                 475                 480

Ile Lys Gln Tyr Gly Phe Val Asp Tyr Asn Phe Thr Ile Val Ala Met
                485                 490                 495

Ala Thr Ile His Gln Val Pro Ser Glu Ser Thr Pro Leu Leu Gly Ala
            500                 505                 510

Ser Leu Arg Gly Asn Lys Arg Thr Lys Leu Ile Gly Leu Ser Tyr Gly
        515                 520                 525

Ala Gly Gly Lys Trp Glu Thr Val Tyr Asp Gly Thr Lys Thr Val Gln
    530                 535                 540

Gly Gly Thr Trp Glu Pro Gly Arg Glu Tyr Gln Val Ala Leu Met Leu
545                 550                 555                 560

Gln Asp Gly Asn Lys Gly Phe Val Tyr Val Asp Gly Val Leu Val Gly
                565                 570                 575

Asn Pro Ala Met Leu Pro Thr Pro Glu Glu Arg Trp Thr Glu Phe Ser
            580                 585                 590

His Phe Tyr Phe Gly Gly Asp Glu Gly Asp Ser Gly Ser Asp Ala Thr
        595                 600                 605

Leu Thr Asp Val Phe Leu Tyr Asn Arg Pro Leu Ser Val Gly Glu Leu
    610                 615                 620

Lys Met Ile Lys Glu Val Glu Asp Leu Glu His His His His His His
625                 630                 635                 640

His His
```

```
<210> SEQ ID NO 5
<211> LENGTH: 1920
<212> TYPE: DNA
<213> ORGANISM: Artificial Sequence
<220> FEATURE:
<223> OTHER INFORMATION: nucleic acid encoding synthetic recombinant
      protein based on TSA1 from T. cruzi
```

<400> SEQUENCE: 5

```
atggaacgta acagtggcga tctgcagctg ccgcaagaaa ttgcgatgct ggtgccgaat      60
aaaacccagg tggttccgaa aagcggcggt gaaggcaaag ttaaagatat cttcgcatct     120
ccggctctgg ttcgtgcagg cggtgtcatg atcgcttttg tggaaggccg caccaaaaac     180
aaactgttcc cggaagttat cgatctgagc tctagtgaca ttgtcgcggg ttatatcaaa     240
gccccggaaa cctggcagag cctggtcgca gaagtgacca aagaatactg gcaagcgcat     300
acggtgctgg aatcggccaa caatagcaac catcgcgtcg gcgtggctcg tctgccgacc     360
ggtattacgc gcggtaataa agtgtttctg ctggttggta gctatgaaga acgtcgcgaa     420
attgatgact acatctggaa agcagaagct tggaacatta aagtcatcga aggcgaagcc     480
acccagtcta cggaagtgca gccgacccaa ccgattaatt ggtcagaacc gaaaccgctg     540
tttcaaaccg attcgccgaa caataaaggc gacctgaaag aattcctggg cggtggcggt     600
agcggtatcg ttatgggcaa cggtaccctg gtctttccgc tgacggcaaa agatgaatcc     660
aataaagtgt tctcactgat tacctattcg acggatgacg gccagaaatg ggaaattccg     720
ggcggtgttt cctcagtcgc aagccgtagc ccgcgcgtta ccgaatggga agaaggtacc     780
ctgctgatgg tgacgtacag cgaagatggc cgtaaagttt ttgaatctcg cgacatgggt     840
aaaacctgga ccgaagcctt tggtaccctg ccgggtgtgt ggctgaaaag cggcccggaa     900
ctgccggaag tctctctgcg tgtggatgcg ctgattaccg ccacgatcga aggtcgtaaa     960
gttatgctgt atacccagaa agtgcgccat tttctggaag ttgatgaacc gaatgccctg    1020
cacctgtggg ttaccgacaa caatcgcacg tttcatctgg gcccgttctc agtcgatagc    1080
gcggaaaaca aaaccttcgc caatacgctg ctgtattcgg atgacgcact gcatctgctg    1140
caggctaaag gtgaccacga atctaccgca gtgagtctgg ctcgtctgac cgaagaactg    1200
aacacgatta attccgttct gtcaacctgg gtccaactgg atgcatcctt ttcagaatcg    1260
agcatcccga ccgctggcct ggttggtttc ctgagcaaca ccacgtctag tggcgatacc    1320
tggattgacg gttatcgcag catgaacgca accgtcacga aagcggccaa agtggaaaat    1380
ggctttaaat tcaccggtcc gggtagtcgt gctacctggc cggtgaactc ccgctgggat    1440
atcaaacagt atggttttgt ggactacaat ttcaccattg ttgcgatggc cacgatccac    1500
caagttccga gcgaaagcac cccgctgctg ggtgccagtc tgcgtggtaa taaacgcacg    1560
aaactgattg gcctgtccta tggtgccggc ggtaaatggg aaaccgtcta cgatggcacc    1620
aaaaccgtgc agggcggtac ctgggaaccg ggtcgtgaat atcaggtggc gctgatgctg    1680
caagatggca acaaaggttt tgtttacgtc gacggcgtgc tggttggtaa tccggccatg    1740
ctgccgaccc cggaagaacg ttggacggaa tttagtcatt tttatttcgg cggtgatgaa    1800
ggcgactctg gtagtgatgc gaccctgacg gacgtcttcc tgtacaaccg cccgctgtcc    1860
gtgggtgaac tgaaaatgat caaagaagtt gaagatcatc atcatcatca tcatcatcat    1920
```

<210> SEQ ID NO 6
<211> LENGTH: 633
<212> TYPE: DNA
<213> ORGANISM: Artificial Sequence
<220> FEATURE:
<223> OTHER INFORMATION: nucleic acid sequence endocing synthetic recombinant protein based on TSA1 from T. cruzi

<400> SEQUENCE: 6

```
atgggtgctt gtgggtcgaa gggctcgacg agcgacaagg ggttggcgag cgataaggac      60
```

```
ggcaagaacg ccaaggaccg caaggaagcg tgggagcgca ttcgccaggc gattcctcgt    120

gagaagaccg ccgaggcaaa acagcgccgc atcgagctat tcaagaagtt cgacaagaac    180

gagactggga agctgtgcta cgatgaggtg cacagcggct gcctcgaggt gctgaagttg    240

gacgagttca cgccgcgagt gcgcgacatc acgaagcgtg cgttcgacaa ggcgagggcc    300

ctgggcagca agctggagaa caagggctcc gaggactttg ttgaatttct ggagttccgt    360

ctgatgctgt gctacatcta cgacttcttc gagctgacgg tgatgttcga cgagattgac    420

gcctccggca acatgctggt cgacgaggag gagctcaagc gcgccgtgcc caagcttgag    480

gcgtggggcg ccaaggtcga ggatcccgcg gcgctgttca aggagctcga taagaatggc    540

actgggtccg tgacgttcga cgagtttgca gcgtgggctt ctgcagtcaa actggacgcc    600

gacggcgacc cggacaacgt gccggagagc gcg                                 633
```

```
<210> SEQ ID NO 7
<211> LENGTH: 633
<212> TYPE: DNA
<213> ORGANISM: Artificial Sequence
<220> FEATURE:
<223> OTHER INFORMATION: nucleic acid sequence encoding synthetic
      recombinant protein based on TSA1 from T. cruzi

<400> SEQUENCE: 7

atgggtgctt gtggctccaa aggttcaacg agtgataaag gtctggcttc ggataaagat     60

ggtaaaaatg ctaaagatcg caaagaagcg tgggaacgta ttcgccaggc catcccgcgt    120

gaaaaaaccg cggaagccaa acaacgtcgc atcgaactgt tcaaaaaatt cgataaaaac    180

gaaacgggca aactgtgcta tgacgaagtg catagcggtt gtctggaagt tctgaaactg    240

gatgaattca ccccgcgtgt ccgcgatatc acgaaacgtg cctttgacaa agcacgcgct    300

ctgggcagca aactggaaaa caaaggttct gaagatttcg tggaattcct ggaatttcgt    360

ctgatgctgt gctatattta cgactttttc gaactgaccg ttatgttcga tgaaatcgac    420

gcaagcggca acatgctggt cgatgaagaa gaactgaaac gcgcggtgcc gaaactggaa    480

gcatggggtg ctaaagttga agatccggcg gccctgttta aagaactgga caaaaatggc    540

accggtagtg ttacgttcga tgaatttgca gcttgggcgt ccgccgtcaa actggatgca    600

gacggcgacc cggataatgt cccggaatca gcc                                 633
```

```
<210> SEQ ID NO 8
<211> LENGTH: 633
<212> TYPE: DNA
<213> ORGANISM: Artificial Sequence
<220> FEATURE:
<223> OTHER INFORMATION: nucleic acid sequence encoding synthetic
      recombinant protein based on TSA1 from T. cruzi

<400> SEQUENCE: 8

atgggtgcta gcggctccaa aggttcaacg agtgataaag gtctggcttc ggataaagat     60

ggtaaaaatg ctaaagatcg caaagaagcg tgggaacgta ttcgccaggc catcccgcgt    120

gaaaaaaccg cggaagccaa acaacgtcgc atcgaactgt tcaaaaaatt cgataaaaac    180

gaaacgggca aactgagcta tgacgaagtg catagcggta gcctggaagt tctgaaactg    240

gatgaattca ccccgcgtgt ccgcgatatc acgaaacgtg cctttgacaa agcacgcgct    300

ctgggcagca aactggaaaa caaaggttct gaagatttcg tggaattcct ggaatttcgt    360

ctgatgctga gctatattta cgactttttc gaactgaccg ttatgttcga tgaaatcgac    420

gcaagcggca acatgctggt cgatgaagaa gaactgaaac gcgcggtgcc gaaactggaa    480
```

gcatggggtg ctaaagttga agatccggcg gccctgttta aagaactgga caaaaatggc 540
accggtagtg ttacgttcga tgaatttgca gcttgggcgt ccgccgtcaa actggatgca 600
gacggcgacc cggataatgt cccggaatca gcc 633

<210> SEQ ID NO 9
<211> LENGTH: 211
<212> TYPE: PRT
<213> ORGANISM: Trypanosoma cruzi

<400> SEQUENCE: 9

Met Gly Ala Cys Gly Ser Lys Gly Ser Thr Ser Asp Lys Gly Leu Ala
1 5 10 15

Ser Asp Lys Asp Gly Lys Asn Ala Lys Asp Arg Lys Glu Ala Trp Glu
20 25 30

Arg Ile Arg Gln Ala Ile Pro Arg Glu Lys Thr Ala Glu Ala Lys Gln
35 40 45

Arg Arg Ile Glu Leu Phe Lys Lys Phe Asp Lys Asn Glu Thr Gly Lys
50 55 60

Leu Cys Tyr Asp Glu Val His Ser Gly Cys Leu Glu Val Leu Lys Leu
65 70 75 80

Asp Glu Phe Thr Pro Arg Val Arg Asp Ile Thr Lys Arg Ala Phe Asp
85 90 95

Lys Ala Arg Ala Leu Gly Ser Lys Leu Glu Asn Lys Gly Ser Glu Asp
100 105 110

Phe Val Glu Phe Leu Glu Phe Arg Leu Met Leu Cys Tyr Ile Tyr Asp
115 120 125

Phe Phe Glu Leu Thr Val Met Phe Asp Glu Ile Asp Ala Ser Gly Asn
130 135 140

Met Leu Val Asp Glu Glu Glu Leu Lys Arg Ala Val Pro Lys Leu Glu
145 150 155 160

Ala Trp Gly Ala Lys Val Glu Asp Pro Ala Ala Leu Phe Lys Glu Leu
165 170 175

Asp Lys Asn Gly Thr Gly Ser Val Thr Phe Asp Glu Phe Ala Ala Trp
180 185 190

Ala Ser Ala Val Lys Leu Asp Ala Asp Gly Asp Pro Asp Asn Val Pro
195 200 205

Glu Ser Ala
210

<210> SEQ ID NO 10
<211> LENGTH: 211
<212> TYPE: PRT
<213> ORGANISM: Artificial Sequence
<220> FEATURE:
<223> OTHER INFORMATION: synthetic recombinant protein based on TSA1 from T. cruzi

<400> SEQUENCE: 10

Met Gly Ala Ser Gly Ser Lys Gly Ser Thr Ser Asp Lys Gly Leu Ala
1 5 10 15

Ser Asp Lys Asp Gly Lys Asn Ala Lys Asp Arg Lys Glu Ala Trp Glu
20 25 30

Arg Ile Arg Gln Ala Ile Pro Arg Glu Lys Thr Ala Glu Ala Lys Gln
35 40 45

Arg Arg Ile Glu Leu Phe Lys Lys Phe Asp Lys Asn Glu Thr Gly Lys
50 55 60

-continued

```
Leu Ser Tyr Asp Glu Val His Ser Gly Ser Leu Glu Val Leu Lys Leu
65                  70                  75                  80

Asp Glu Phe Thr Pro Arg Val Arg Asp Ile Thr Lys Arg Ala Phe Asp
                85                  90                  95

Lys Ala Arg Ala Leu Gly Ser Lys Leu Glu Asn Lys Gly Ser Glu Asp
            100                 105                 110

Phe Val Glu Phe Leu Glu Phe Arg Leu Met Leu Ser Tyr Ile Tyr Asp
        115                 120                 125

Phe Phe Glu Leu Thr Val Met Phe Asp Glu Ile Asp Ala Ser Gly Asn
    130                 135                 140

Met Leu Val Asp Glu Glu Glu Leu Lys Arg Ala Val Pro Lys Leu Glu
145                 150                 155                 160

Ala Trp Gly Ala Lys Val Glu Asp Pro Ala Ala Leu Phe Lys Glu Leu
                165                 170                 175

Asp Lys Asn Gly Thr Gly Ser Val Thr Phe Asp Glu Phe Ala Ala Trp
            180                 185                 190

Ala Ser Ala Val Lys Leu Asp Ala Asp Gly Asp Pro Asp Asn Val Pro
        195                 200                 205

Glu Ser Ala
    210


<210> SEQ ID NO 11
<211> LENGTH: 8
<212> TYPE: PRT
<213> ORGANISM: Artificial Sequence
<220> FEATURE:
<223> OTHER INFORMATION: Synthetic histidine tag

<400> SEQUENCE: 11

His His His His His His His His
1               5
```

CHAGAS DISEASE VACCINE ANTIGENS WITH IMPROVED STABILITY AND DECREASED AGGREGATION

SEQUENCE LISTING

This application includes as the Sequence Listing the complete contents of the accompanying text file "Sub_sequence_listing_15060001US", created Jan. 10, 2025, containing 32,895 bytes, hereby incorporated by reference.

BACKGROUND OF THE INVENTION

Field of the Invention

This invention generally relates to the prevention and treatment of Chagas disease. In particular, the invention provides vaccine antigens against Chagas disease comprising recombinant *Trypanosoma cruzi* TSA-1-derived proteins with improved solubility properties and excellent in vivo efficacy.

State of Technology

Chagas disease (American trypanosomiasis) is a serious disease caused by infection with the protozoan *Trypanosoma cruzi*, which is primarily transmitted by the bite of the triatomine insect vector (the "kissing bug"). However, in addition to insects, the transmission of the pathogen may be spread through blood transfusion, organ transplantation, ingesting contaminated food, or by vertical transmission from mother to child. About 10 million people are infected worldwide, and tragically, about 30-40% of infected patients develop chronic Chagasic cardiomyopathy which ultimately leads to cardiac failure and death. Due to the limited efficacy and side effects of currently available drugs, developing a vaccine to prevent the infection and/or reduce the effects of the disease is urgent.

The TSA1 protein is a 835-amino acid surface transsialidase of *T. cruzi* and is a leading vaccine antigen that has exhibited both preventive and therapeutic efficacy against *T. cruzi* infection in mouse models when tested as a DNA vaccine. This protection is associated with increased levels of parasite-specific IFN-gamma producing CD4+ and CD8+ T cells in the spleen and in infected cardiac tissue.

For use in humans, a protein-based vaccine is preferable due to efficacy, safety and regulatory concerns regarding DNA vaccines. However, neither full length TSA1 protein nor a C-terminal fragment thereof (aa 618-834) conferred protection against *T. cruzi* challenge when tested in mice (Wrightsman et al. *J Immunol* 1994; 153:3148-3154). However, 70% of the mice immunized with the amino-proximal portion of TSA-1 survived challenge.

There is an urgent need in the art for recombinant proteins which exhibit high antigenicity against *T. cruzi* but which are suitable for the preparation of vaccine composition.

SUMMARY OF THE INVENTION

The present disclosure provides new TSA-1-based mutant recombinant proteins to treat and/or provide protection against *T. cruzi* infection. Advantageously, the recombinant proteins are engineered (designed) so that they do not aggregate during storage. Data presented in the Examples section below demonstrate that the recombinant proteins remain soluble during storage, exhibit excellent antigenicity and are protective against the *T. cruzi* parasite. Pharmaceutical compositions comprising the TSA-1-based recombinants are also provided, as are pharmaceutical compositions comprising the TSA-1-based recombinants and one or more additional recombinants proteins/polypeptides, e.g. derived from other *T. cruzi* antigenic proteins such as Tc24.

It is an object of the invention to provide a recombinant protein comprising SEQ ID NO: 1, wherein X1, X2, X3 and X4 are Cys, Ser, Thr or Met, and wherein at least one of X1, X2, X3 and X4 is not Cys. In some aspects, 2, 3, or 4 of X1, X2, X3 and X4 are not Cys. In further aspects, X1, X2, X3 and X4 are Ser. In other aspects, the recombinant protein comprises a C-terminal histidine tag.

Also provided are compositions comprising a recombinant protein comprising SEQ ID NO: 1, wherein X1, X2, X3 and X4 are Cys, Ser, Thr or Met, and wherein at least one of X1, X2, X3 and X4 is not Cys. In some aspects, 2, 3, or 4 of X1, X2, X3 and X4 are not Cys. In further aspects, X1, X2, X3 and X4 are Ser. In other aspects, the recombinant protein comprises a C-terminal histidine tag. In further aspects, the compositions include the recombinant protein of SEQ ID NO: 7. In additional aspects, the compositions comprise an adjuvant. In some aspects, the adjuvant is monophosphoryl lipid A (MPLA).

Also provided is a method of treating or preventing at least one symptom of a *Trypanosoma cruzi* infection in a subject in need thereof, comprising administering to the subject a therapeutically effective amount of a composition comprising a recombinant protein comprising SEQ ID NO: 1, wherein X1, X2, X3 and X4 are Cys, Ser, Thr or Met, and wherein at least one of X1, X2, X3 and X4 is not Cys. In some aspects, 2, 3, or 4 of X1, X2, X3 and X4 are not Cys. In further aspects, X1, X2, X3 and X4 are Ser. In other aspects, the recombinant protein comprises a C-terminal histidine tag. In further aspects, the compositions include the recombinant protein of SEQ ID NO: 7. In additional aspects, the compositions comprise an adjuvant. In some aspects, the adjuvant is monophosphoryl lipid A (MPLA). In some aspects, the subject is a human, horse, cow, dog, cat, goat, sheep, or pig. In further aspects, the method includes a step of diagnosing the *T. cruzi* infection. In additional aspects, the at least one symptom of a *Trypanosoma cruzi* infection is a symptom of acute infection or a symptom of chronic infection. In yet further aspects, the symptom of acute infection is one or more of: swelling at the infection site, fever, fatigue, rash, body aches, eyelid swelling, headache, loss of appetite, swollen glands and enlargement of the liver or spleen. In other aspects, the symptom of chronic infection is one or more of: irregular heartbeat, congestive heart failure, sudden cardiac arrest, difficulty swallowing due to an enlarged esophagus, and abdominal pain or constipation due to enlarged colon. In additional aspects, the method further comprises administering benznidazole to the subject.

Also provided is a method of decreasing the number of inflammatory cells in heart tissue of a subject infected with *T. cruzi*, comprising administering to the subject a therapeutically effective amount of a composition comprising a recombinant protein comprising SEQ ID NO: 1, wherein X1, X2, X3 and X4 are Cys, Ser, Thr or Met, and wherein at least one of X1, X2, X3 and X4 is not Cys. In some aspects, 2, 3, or 4 of X1, X2, X3 and X4 are not Cys. In further aspects, X1, X2, X3 and X4 are Ser. In other aspects, the recombinant protein comprises further a C-terminal histidine tag. In further aspects, the compositions include the recombinant protein of SEQ ID NO: 7.

Other features and advantages of the present invention will be set forth in the description of invention that follows, and in part will be apparent from the description or may be learned by practice of the invention. The invention will be realized and attained by the compositions and methods particularly pointed out in the written description and claims hereof.

BRIEF DESCRIPTION OF THE DRAWINGS

FIG. 1. Generic recombinant protein with positions 248, 267, 360 and 438 represented by X and shaded (SEQ ID NO: 1); 43 amino acid fragment added to complete the second domain at the carboxy terminus is underlined.

FIG. 2. Amino acid sequence alignment of TSA-1-NT (SEQ ID NO: 2) and an exemplary recombinant TSA-1-C4 (SEQ ID NO: 3) with C248, C267, C360, C447 mutated to serine(S) (grey shaded). Methionine (M) at position 1 is expressed from the vector.

FIGS. 5A and B. A, amino acid sequence of TSA-1-C4+a histidine (His) tag (SEQ ID NO: 11); mutated residues are C248S, C267S, C360S and C447S; B, TSA-1-C4 without a His-tag (SEQ ID NO: 3).

DETAILED DESCRIPTION

Figure 3A:
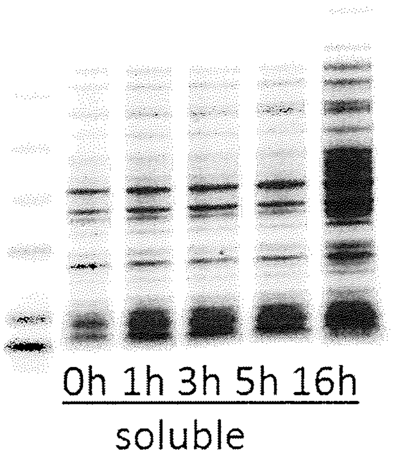
FIGS. 3A and B. SDS-PAGE of expressed wild-type TSA-1-NT in *E. coli* BL21 (DE3) induced with 0.5 mM IPTG from 0-16 hours. A, soluble protein; B, inclusion body staining.

An N-terminal fragment of TSA-1 (TSA-1-NT, aa 30-617; shown as SEQ ID NO: 2 in FIG. 2) induces protective immunity in mice, suggesting that in the full-length protein the C-terminal fragment of TSA-1 may mask the protective epitope(s) at the N-terminus. Thus, TSA-1-NT appeared to be a promising vaccine candidate. Unfortunately, when compounded into vaccine compositions, TSA-1-NT aggregates, making it unsuitable for long-term storage and use in vaccine compositions. To address this issue, the present invention provides recombinant proteins based on TSA-1 but which are soluble and thus suitable for use in vaccines.

The design of the TSA-1-based recombinant proteins disclosed herein is based on the following: the amino acid sequence of the TSA-1 fragment TSA-1-NT (SEQ ID NO: 2 in FIG. 3) includes cysteine (Cys) residues at 4 positions: residues 248, 267, 360 and 438. Without being bound by theory it is believed that when TSA-1-NT is in solution in vitro, disulfide bridges form between at least two of the cysteines (e.g. within and between protein chains) forming dimers, trimers, etc. and causing the TSA-1-NT to aggregate and/or precipitate. In the recombinant proteins provided herein, the Cys residues have been replaced, by conservative substitution, with an amino acid that is not capable of forming inter- or intramolecular disulfide bonds. The resulting recombinant fragments do not aggregate in solution, even upon extended storage at 4° C. In addition, these recombinant fragments also exhibit excellent antigenicity and evoke protection against the development of symptoms of *T. cruzi* infection in vivo. Thus, cysteine mutagenesis improved production without abrogating antigenicity.

SEQ ID NO: 1 of FIG. 1 depicts an exemplary generic TSA-1-based recombinant protein as disclosed herein. In SEQ ID NO: 1, the first 589 amino acids correspond to residues 30-330 of the parent *T. cruzi* TSA-1 protein (UniProtKB—Primary (citable) accession number: Q26971), similar to TSA1-NT. However, in SEQ ID NO: 1, the shaded amino acids at positions 248, 267, 360 and 438 are represented by X1, X2, X3 and X4. In the native protein, and in TSA-1-NT, the corresponding residues are Cys. In the recombinant mutant proteins, at least one of the residues represented by "X" is not Cys but is an amino acid that cannot readily form a covalent bond, such as Ser, Thr or Met. Generally, at least 1, 2, 3 or all 4 of those positions are not Cys. In some exemplary aspects, Ser replaces Cys at all four positions e.g. as in the exemplary recombinant protein TSA-1-C4 (SEQ ID NO: 3 in FIG. 2).

In addition, in some aspects, a second 43-amino acid peptide fragment corresponding to residues 618-660 of TSA-1 of *Trypanosoma cruzi* is also included in the present recombinants (underlined sequence in SEQ ID NO: 1, FIG. 1, and residues 659 to 632 of SEQ ID NO: 3 in FIG. 2). Without being bound by theory, is believed that this fragment complete the second domain confers additional stability and solubility to the recombinants.

Accordingly, the present disclosure provides mutant, recombinant TSA-1-based proteins/polypeptides and immunogenic compositions (such as vaccine preparations) comprising the mutants that are amenable to storage and thus can be used in methods of preventing and/or treating a disease caused by *T. cruzi* infection, such as Chagas disease in humans. Methods of making the recombinants and compositions containing the recombinants are also encompassed. The amino acid sequence of the recombinant proteins comprises several modifications or changes compared to the corresponding residues of the TSA-1 protein as found in nature. Thus, the recombinants are non-natural or "artificial". The modification(s) are at least present at one or more of the four cysteine residues that likely cause intermolecular disulfide bridges and protein aggregation during purification and/or storage of the native protein and the TSA-1-NT fragment. The disclosed mutant can advantageously be stored at low temperatures e.g. at 2° C., for prolonged periods of time, e.g. at least for several weeks or months.

Definitions

The following definitions are used throughout:

Chagas disease stages and symptoms thereof: There are three stages of infection with Chagas disease: acute (indeterminant) and chronic (both determinant and intetermінant). These generally recognized categories are distinguished as follows:

Acute: Acute symptoms only occur in about 1% of cases and most people infected do not seek medical attention. The most recognized symptom of acute Chagas infection is the "Romaña's sign" or swelling of the eye on one side of the face, usually at the bite wound or where insect feces were rubbed into the eye. Other symptoms are usually not specific for Chagas infection and may include fatigue, fever, enlarged liver or spleen, and swollen lymph glands. Sometimes, a rash, loss of appetite, diarrhea, and vomiting occur. In infants and in very young children with acute Chagas disease, swelling of the brain can develop and this can cause death. In general, symptoms last for 4-8 weeks and then dissipate, even without treatment.

Indeterminant: Eight to 10 weeks after infection, the indeterminate stage begins. During this stage, people do not have symptoms.

Chronic: Approximately 10 to 20 years after infection, people may develop the most serious symptoms of Chagas disease. Cardiac problems, including an enlarged heart, altered heart rate or rhythm, heart failure, or cardiac arrest are symptoms of chronic disease. Chagas disease can also lead to enlargement of parts of the digestive tract, which result in severe constipation or problems with swallowing. In persons who are immune compromised, including persons with HIV/AIDS, Chagas disease can be severe. All infected persons do not develop chronic disease.

The terms "protein", "polypeptide" and "peptide" refer to contiguous chains of amino acids that are covalently bonded (linked) to each other by peptide (amide) bonds. In general, a peptide contains up to about 50 amino acids and a polypeptide contains about 50 or more amino acids. Proteins may contain one or more than one polypeptide. Those of skill in the art will recognize that these definitions are considered somewhat arbitrary, and these terms may be used interchangeably herein. The terms encompass amino acid polymers that are synthesized (transcribed and translated) in vivo and amino acid polymers that are chemically synthesized using procedures well known to those skilled in the art.

As used herein, the terms "nucleic acid" or "polynucleotide" or "nucleic acid molecule" refer to deoxyribonucleotides or ribonucleotides and polymers thereof in either single- or double-stranded form. Exemplary nucleic acids include DNA (including cDNA), RNA (e.g. mRNA, RNA, rRNA, etc.), and hybrids thereof.

The term "gene" means a segment of DNA that encodes a biologically active RNA, which may be further translated into a polypeptide chain. The term may or may not include regions preceding and following the coding region as well as intervening sequences (introns) between individual coding segments (exons). As used herein, a gene may be a recombinant or genetically engineered DNA sequence that encodes a polypeptide of interest from which introns have been eliminated.

The terms "similarity" and "identity" are known in the art. Generally, "identity" refers to a sequence comparison based on identical matches between corresponding identical positions in the sequences being compared. "Similarity" refers to a comparison between sequences and takes into account not only identical positions, but also those which are functionally similar Percentages of "similarity", "identity" and "homology" between or among sequences may be determined by various tools that are readily available to those of skill in the art. For example, see issued U.S. Pat. No. 8,507,650 (Gabriel, et al.) and references cited therein, the complete contents of which is hereby incorporated by referenced in entirety.

As used herein, the term "heterologous" refers to e.g. polypeptide, nucleic acid, promoter, etc. that originates from a source foreign to a particular host cell. The particular host cell in which the heterologous (non-native) polypeptide, nucleic acid, etc. is expressed may be referred to as a "heterologous" host cell. The term "heterologous" may also be used to refer to a genetic element which does not occur in nature as being operably linked to other genetic elements. For example, a promoter may be referred to a as being heterologous to a operably linked coding region when that promoter and coding region are not occurring as being operably linked in nature.

As used herein, a DNA segment is referred to as "operably linked" when it is placed into a functional relationship with another DNA segment. For example, DNA for a signal sequence is operably linked to DNA encoding a polypeptide if it is expressed as a preprotein that participates in the secretion of the polypeptide; a promoter or enhancer is operably linked to a coding sequence if it stimulates the transcription of the sequence. Generally, DNA sequences that are operably linked are contiguous, and in the case of a signal sequence both contiguous and in reading phase.

However, enhancers need not be contiguous with the coding sequences whose transcription they control. Linking is accomplished by ligation at convenient restriction sites or at adapters or linkers inserted in lieu thereof.

As used herein, the term "transformation" refers to the transfer of nucleic acid (i.e., a nucleotide polymer) into a cell. As used herein, the term "genetic transformation" refers to the transfer and incorporation of DNA, especially recombinant DNA, into a cell. The term "transformant" refers to a cell, tissue or organism that has undergone transformation.

As used herein, the term "transgenic" refers to cells, cell cultures, organisms (e.g., plants), and progeny which comprise a modified or foreign (heterologous) gene, wherein the modified or foreign gene is not originally present in the host organism. Transgenic organisms may receive the foreign gene by one of the various methods of transformation, but may also receive the transgene via conventional breeding techniques whereby at least one of the parent organisms comprises such a transgene.

"Recombinant" refers to a product of genetic engineering, e.g. a nucleic acid such as recombinant DNA, a protein that results from the expression of recombinant DNA, and recombinant cells or organisms that are transformed with recombinant DNA.

Recombinant Proteins/Polypeptides

The recombinant proteins described herein comprise one or more modifications compared to native, wild type TSA-1 protein. Firstly, in general, the recombinants comprise residues corresponding approximately to a fragment of native TSA-1, namely residues 618-834. While these residues are typically included, those of skill in the art will recognize that it may be possible to exclude and/or add certain TSA-1 residues at the amino or carboxyl terminus of this fragment, or internally within the fragment, without decreasing the favorable solubility and antigenic activity of the recombinants. For example, e.g. 20 amino acids or less may be omitted or added, such as about 20, 19, 18, 17, 16, 15, 14, 13, 12, 11, 10, 9, 8, 7, 6, 5, 4, 3, 2, or 1 amino acid(s) may be omitted (deleted) from or added to the carboxy and/or amino termini of the sequences disclosed herein, or one or more internals deletions or additions may be made, as long as the resulting sequence retains the disclosed solubility and antigenicity. If sequences are added at the termini, they may be additional sequences derived from the parent TSA-1 protein, such as amino acids that are immediately adjacent to the fragment. Typically, all the residues corresponding to residues 618-834 of TSA-1 are included in each recombinant. Also, typically an N-terminal Met residue, derived from an encoding vector, is present.

In the recombinants, at least one of the Cys residues that are present in native TSA-1 is changed/replaced by an amino acid with a side chain that does not, or does not readily, form a covalent bond with a side chain of another amino acid, such as another amino acid within the recombinant, or with another amino acid present on another recombinant when multiple proteins are present in a composition. Also, the amino acids that replace Cys have properties similar to those of Cys in that they are typically uncharged at physiologically relevant pH values (e.g. from about pH 6.5 to about pH 7.5); they have similarly sized side chains, e.g. they are not bulky or highly hydrophobic, etc.; and they are capable of adopting configurations and conformations that do not obscure or block the epitopes (antigenic determinants) that are present in the full sequence, i.e. the epitopes that elicit an immune response are maintained. Suitable amino acids that may replace or substitute for a Cys include but are not limited to: Ser, Thr and Met, although replacement by other amino acids is not excluded, e.g. Ala, Gly, etc. Generally, the modification(s) are at least present at one of the four cysteine residues and may be present at 1, 2, 3 or all 4 of the Cys residues.

In some aspects, the recombinants also include, at the carboxy terminus, approximately 43 amino acids derived from the TSA-1 of *T. cruzi* after a 3D homology modeling using a transialidasas 3D structure from *T. rangeli* as template. An example of this sequence is: EFSHFYFGGDE-GDSGSDATLTDVFLYNRPLSVGELKMIKEVED (SEQ ID NO: 4). However, those of skill in the art will recognize that it may be possible to exclude or add certain residues at the amino or carboxyl terminus of this fragment, or internally within the fragment, without decreasing the desired activity of this sequence (e.g. increasing solubility and/or stability of the sequence).

Various modifications of the sequences disclosed herein (variants or derivatives) are also encompassed, e.g. various replacements or substitutions, in addition to those of Cys residues. For example, a Met residue (generally derived from a vector) may or may not be present at the amino terminus. In addition, various conservative or non-conservative amino acid substitutions throughout the sequences may be tolerated, as long as the activity and properties of the sequences disclosed herein are retained. In the context of the present invention, a "conservative substitution" refers to substitutions within the classes of amino acids such as: aliphatic residues I, L, V, and M; cycloalkenyl-associated residues F, H, W, and Y; hydrophobic residues A, C, F, G, H, I, L, M, R, T, V, W, and Y; negatively charged residues D and E; polar residues C, D, E, H, K, N, Q, R, S, and T; positively charged residues H, K, and R; small residues A, C, D, G, N, P, S, T, and V; very small residues A, G, and S; and flexible residues Q, T, K, S, G, P, D, E, and R. Additional conservative substitutions groupings include: valine-leucine-isoleucine, phenylalanine-tyrosine, lysine-arginine, alanine-valine, and asparagine-glutamine. Conservation in terms of hydropathic/hydrophilic properties and residue weight/size also is substantially retained in the polypeptides of the present invention as compared to the native sequence and/or the specific sequences disclosed herein.

Other modifications may be made for any purpose, such as to increase immunogenicity, to improve folding, to enhance purification, to increase storage length, to reduce aggregation, and a combination thereof. Examples of modifications include amino acid substitution, deletion, inversion, addition, truncation (C-terminal and/or N-terminal), and so forth. When amino acid(s) are substituted, the substitution may or may not be conservative. In cases wherein the cysteine residue(s) are substituted, the substitution may or may not be conservative. However, to encourage proper folding, the substitutions at cysteine may be to serine, methionine, or threonine. In a given recombinant polypeptide, when multiple cysteines are mutated they may or may not be substituted with the same amino acid.

It also is understood in the art that the substitution of like amino acids can be made effectively on the basis of hydrophilicity, as described in U.S. Pat. No. 4,554,101, incorporated herein by reference. In making changes based upon similar hydrophilicity values, the substitution of amino acids whose hydrophilicity values are within +2 is preferred, those which are within +1 are particularly preferred, and those within +0.5 are even more particularly preferred.

Thus, sequences which exhibit at least about 80% identity or similarity to the sequences disclosed herein are encompassed, e.g. sequences with about 80, 85, 90, 91, 92, 93, 94, 95, 96, 97, 98 or 99% identity or similarity, when compared using standard alignment techniques that are known in the art, are included. Exemplary additional mutations which may be present include but are not limited to: changes which introduce or eliminate sequences susceptible to proteolysis; various "tagging" sequences which may be used to identify and/or to isolate the recombinants, e.g. His tags, Human influenza hemagglutinin (HA) tag, etc.; incorporation of one or more so-called "non-natural" amino acids, amino acid derivatives or amino acid mimics; etc. All such possible variants or derivatives of the recombinants disclosed herein are encompassed by the present invention, as long as the variants are immunologically functional equivalents of the disclosed proteins, having the same (or better) utility and biological activity, and are soluble upon storage at low temperatures (e.g. about 2-8° C., such as about 5° C.) for extended periods of time, e.g. at least about 1, 2, 3, 4, 5, 6, 7, 8. 9 or 10 weeks, or for several months, e.g. 1, 2, 3, 4, 5 or 6 months or longer.

Changes made to the TSA-1-based antigens disclosed herein may be made for any reason such as, for example, reducing aggregation, enhancing its immunogenicity and/or producing or identifying a immunologically functional equivalent sequence. Methods of mutagenesis are well known to those of skill in the art (Sambrook et al., 1987). Examples include but are not limited to: "oligonucleotide directed mutagenesis" (both template-dependent processes and vector-mediated propagation); site directed mutagenesis e.g. site-specific mutagenesis, including alanine scanning mutagenesis and methods disclosed in U.S. Pat. Nos. 5,220,007; 5,284,760; 5,354,670; 5,366,878; 5,389,514; 5,635,377; and 5,789,166. Any of these methods may be utilized to effect the variations discussed herein.

The polypeptides may also include various labels which are known in the art, for example: radioactive isotopes may be incorporated; biotin may be added; the polypeptides may be conjugated to enzymes such as horseradish peroxidase (HRP), alkaline phosphatase (AP), glucose oxidase and β-galactosidase; various fluorescent, chemiluminescent or phosphorescent labels may be attached (e.g. organic dyes such as flurorisothiocyanate (FITC), tetramethylrho-damine isothiocyanate (TRITC) and various rhodamine dyes, DyLight® Fluors for labeling amine or sulfhydryl groups, etc.); biological fluorophore may be used (e.g. Green fluorescent protein (GFP), R-Phycoerythrin; nanoscale-sized (2-50 nm) semiconductors known as "Quantum dots"; various Expressed Sequence Tags (ESTs); etc. In addition, various other sequences of benefit may be appended to the polypeptides, e.g. targeting sequences, leader sequences, and the like.

Further, due to expression in heterologous host systems described below, one or more than one posttranslational modifications may be present in a protein that is produced. Any posttranslational modification may be present on the polypeptide, examples of which include but are not limited to: glycosylation, myristilation, ubiquitination, phosphorylation, acylation, acetylation, alkylation, oxidation, amidation, propionylation, hydroxylation, malonylation, and so forth.

In addition to the peptidyl compounds described herein, the inventors also contemplate that other sterically similar compounds may be formulated to mimic the key portions of the peptide or polypeptide structure or to interact specifically with, for example, an antibody. Such compounds, which may be termed peptidomimetics, may be used in the same manner as a peptide or polypeptide of the invention and hence are also immunologically functional equivalents.

Certain mimetics that mimic elements of protein secondary structure are described in Johnson et al. (1993). The underlying rationale behind the use of peptide mimetics is that the peptide backbone of proteins exists chiefly to orientate amino acid side chains in such a way as to facilitate molecular interactions, such as those of antibody and antigen. A peptide mimetic is thus designed to permit molecular interactions similar to the natural molecule.

Immunologically Functional Equivalents

It is well understood that where certain residues are shown to be particularly important to the immunological or structural properties of a protein or peptide, e.g., residues in epitopes, such residues may not generally be exchanged. Changes at an antigenic site (other than the one or more cysteines that may or may not be at antigenic sites) should be carefully considered and subsequently tested to ensure maintenance of immunological function (e.g., antigenicity). In this manner, functional equivalents are defined herein as those peptides or polypeptides that maintain a substantial amount of their native immunological activity.

Numerous scientific publications have also been devoted to the identification of an epitope, and computer programs are available to assist with predicting antigenic regions. Examples include programs based on the Jameson-Wolf analysis (Jameson & Wolf, 1988; Wolf et al., 1988), the program PepPlot® (Brutlag et al., 1990; Weinberger et al., 1985), and other new programs for protein tertiary structure prediction (Fetrow & Bryant, 1993). Another commercially available software program capable of carrying out such analyses is MacVector (IBI, New Haven, CT). Alternatively, major antigenic determinants may be identified by an empirical approach in which portions of a nucleic acid encoding the polypeptide are expressed in a recombinant host, and the resulting polypeptide(s) tested for their ability to elicit an immune response; or by synthesizing and screening overlapping peptides While discussion has focused on functionally equivalent polypeptides arising from amino acid changes, it will be appreciated that these changes may be effected by alteration of the encoding DNA; taking into consideration also that the genetic code is degenerate and that two or more codons may code for the same amino acid. Nucleic acids encoding these antigenic compositions also can be constructed and inserted into one or more expression vectors by standard methods (Sambrook et al., 1987), for example, using PCR™ cloning methodology.

Nucleic Acids, Vectors and Host Cells

Nucleic Acids

The present invention further provides isolated nucleic acid molecules and their complements that contain genetic sequences (genes) which encode the protein/polypeptide sequences disclosed herein. An exemplary sequence encoding the recombinant TSA-1-C4 is presented below as SEQ ID NO: 5. In SEQ ID NO: 5, the codons for Ser which replace Cys residues are underlined. This sequence is codon optimized for expression in *E. coli* and a His tag is encoded by this exemplary sequence.

```
>TSA1-C4 + His 1896 bp
                                    (SEQ ID NO: 5)
ATGGAACGTAACAGTGGCGATCTGCAGCTGCCGCAAGAAATTGCGATGC

TGGTGCCGAATAAAACCCAGGTGGTTCCGAAAAGCGGCGGTGAAGGCAA

AGTTAAAGATATCTTCGCATCTCCGGCTCTGGTTCGTGCAGGCGGTGTC
```

-continued

ATGATCGCTTTTGTGGAAGGCCGCACCAAAAACAAACTGTTCCCGGAAG

TTATCGATCTGAGCTCTAGTGACATTGTCGCGGGTTATATCAAAGCCCC

GGAAACCTGGCAGAGCCTGGTCGCAGAAGTGACCAAAGAATACTGGCAA

GCGCATACGGTGCTGGAATCGGCCAACAATAGCAACCATCGCGTCGGCG

TGGCTCGTCTGCCGACCGGTATTACGCGCGGTAATAAAGTGTTTCTGCT

GGTTGGTAGCTATGAAGAACGTCGCGAAATTGATGACTACATCTGGAAA

GCAGAAGCTTGGAACATTAAAGTCATCGAAGGCGAAGCCACCCAGTCTA

CGGAAGTGCAGCCGACCCAACCGATTAATTGGTCAGAACCGAAACCGCT

GTTTCAAACCGATTCGCCGAACAATAAAGGCGACCTGAAAGAATTCCTG

GGCGGTGGCGGTAGCGGTATCGTTATGGGCAACGGTACCCTGGTCTTTC

CGCTGACGGCAAAAGATGAATCCAATAAAGTGTTCTCACTGATTACCTA

TTCGACGGATGACGGCCAGAAATGGGAAATTCCGGGCGGTGTTTCCTCA

GTCGCAAGCCGTAGCCCGCGCGTTACCGAATGGGAAGAAGGTACCCTGC

TGATGGTGACGTACAGCGAAGATGGCCGTAAAGTTTTTGAATCTCGCGA

CATGGGTAAAACCTGGACCGAAGCCTTTGGTACCCTGCCGGGTGTGTGG

CTGAAAAGCGGCCCGGAACTGCCGGAAGTCTCTCTGCGTGTGGATGCGC

TGATTACCGCCACGATCGAAGGTCGTAAAGTTATGCTGTATACCCAGAA

AGTGCGCCATTTTCTGGAAGTTGATGAACCGAATGCCCTGCACCTGTGG

GTTACCGACAACAATCGCACGTTTCATCTGGGCCCGTTCTCAGTCGATA

GCGCGGAAAACAAAACCTTCGCCAATACGCTGCTGTATTCGGATGACGC

ACTGCATCTGCTGCAGGCTAAAGGTGACCACGAATCTACCGCAGTGAGT

CTGGCTCGTCTGACCGAAGAACTGAACACGATTAATTCCGTTCTGTCAA

CCTGGGTCCAACTGGATGCATCCTTTTCAGAATCGAGCATCCCGACCGC

TGGCCTGGTTGGTTTCCTGAGCAACACCACGTCTAGTGGCGATACCTGG

ATTGACGGTTATCGCAGCATGAACGCAACCGTCACGAAAGCGGCCAAAG

TGGAAAATGGCTTTAAATTCACCGGTCCGGGTAGTCGTGCTACCTGGCC

GGTGAACTCCCGCTGGGATATCAAACAGTATGGTTTTGTGGACTACAAT

TTCACCATTGTTGCGATGGCCACGATCCACCAAGTTCCGAGCGAAAGCA

CCCCGCTGCTGGGTGCCAGTCTGCGTGGTAATAAACGCACGAAACTGAT

TGGCCTGTCCTATGGTGCCGGCGGTAAATGGGAAACCGTCTACGATGGC

ACCAAAACCGTGCAGGGCGGTACCTGGGAACCGGGTCGTGAATATCAGG

TGGCGCTGATGCTGCAAGATGGCAACAAAGGTTTTGTTTACGTCGACGG

CGTGCTGGTTGGTAATCCGGCCATGCTGCCGACCCCGGAAGAACGTTGG

ACGGAATTTAGTCATTTTTATTTCGGCGGTGATGAAGGCGACTCTGGTA

GTGATGCGACCCTGACGGACGTCTTCCTGTACAACCGCCCGCTGTCCGT

GGGTGAACTGAAAATGATCAAAGAAGTTGAAGATCATCATCATCATCAT

CATCATCAT

While exemplary encoding nucleotide sequences are provided herein, those of skill in the art will recognize that, due to the redundancy of the genetic code, other nucleotide sequences may also encode the same protein/polypeptide. Generally, such sequences are at least about 75, 80, 85, 90, 95, 96, 97, 98 or 99% identical to the disclosed sequences.

Vectors and Host Cells

The invention also encompasses vectors such as cloning vectors that comprise the nucleic acid sequences described herein. "Vector" refers broadly to e.g. any plasmid, cosmid, phagemid or virus encoding an exogenous nucleic acid. There are many types of cloning vectors, but the most commonly used ones are genetically engineered plasmids. Cloning is often first performed using *E. coli*, and cloning vectors in *E. coli* include plasmids, bacteriophages (such as phage 2), cosmids, and bacterial artificial chromosomes (BACs). However, other organisms such as yeast may be used. Cloning vectors in yeast include yeast artificial chromosomes (YACs). In some cases, viral vectors are suitable. Examples of viral vectors include, but are not limited to recombinant vaccinia, adeno-, retro-, adeno-associated, avian pox and other viral vectors.

The gene sequences that encode the recombinant proteins are generally expressed in culture in transgenic prokaryotic or eukaryotic host cells by transformation of the host cell by a vector, and such host cells are also encompassed by the invention. Expression in a host may be transient or stable. The recombinants may be produced in cells that are bacterial, yeast, mammalian, or insect in origin. For example, suitable expression host cells include but are not limited to: prokaryotic bacteria (such as *Escherichia coli* (e.g. those based on *E. coli* BL21 and *E. coli* K12), *Bacillus brevis, Bacillus megaterium, Bacillus subtilis, Caulobacter crescentus*, etc.: yeast (e.g. *Saccharomyces cerevisiae* and *Pichia pastoris*); insect cells (e.g. Baculovirus systems); and mammalian hosts (e.g. those based on HEK293 or CHO cell lines); etc. In some aspects, the host cells are *E. coli* host cells.

The gene that encodes the TSA-1 protein is a eukaryotic gene from *T. cruzi* but the mutant sequences disclosed herein are typically expressed in heterologous expression systems, i.e. the nucleic acid molecules that encode the recombinant protein are derived from a heterologous protein that is not expressed in the transgenic host in nature. Thus, the nucleic acid molecules described herein may be modified, for example, by codon optimization to facilitate expression in heterologous cells. This type of modification changes or alters the nucleotide sequence that encodes a protein of interest so that throughout the sequence, codons that are more-commonly used in the transgenic expression host cell are used. In addition, changes may be made to the nucleotide sequence that adjust the relative concentration of A/T and G/C base pairs to ratios that are more similar to those of the expression host. In addition, the encoding sequences are generally operably linked to a promoter that is suitable for expression within the host cells. Suitable promoters are generally known in the art.

One or more other elements which enhance, control or optimize transcription and/or translation of the sequences within a transgenic host or which are otherwise beneficial include but are not limited to: various enhancer elements (such as various cis-acting elements within the regulatory regions of the DNA), trans-acting factors that include transcription factors; e.g. sequences which target or direct the protein to a particular location or locations within the expression host cell; etc.

The invention also encompasses the transgenic host cells which have been genetically engineered using molecular biology techniques to contain and express nucleic acid molecules encoding the recombinants described herein.

Methods of Making the Recombinant Proteins

The recombinant proteins of the present disclosure may be made by any suitable method. Suitable methods include but are not limited to: by the expression of a nucleic acid sequence (e.g., a DNA sequence) encoding the protein in an in vitro translation system; or in a living cell, e.g. using vectors and host cells as described above; or by solid phase chemical synthesis (which typically also requires purification away from the other products of the chemical reactions e.g. by HPLC). After synthesis, the recombinant proteins are typically isolated and/or purified. For example, they may be subjected to chromatography such as size exclusion chromatography; and/or extensively dialyzed to remove one or more undesired small molecular weight molecules; or if a His or other tag is present, they may be purified by affinity column chromatography, etc. In addition, the proteins may be lyophilized for storage or for ready formulation into a desired vehicle.

A major advantage of the new recombinants disclosed herein is that they do not aggregate appreciably when stored for prolonged periods of time in the cold. In some aspects, a aggregation is assessed by quantifying the % monomer by e.g. SDS-PAGE analysis, HPLC, size exclusion and/or dynamic light scattering. For example, generally at least about 50% or more (e.g. at least about 60, 70, 75, 80, 85, 90, 95 or more) of the recombinant proteins remain monomeric during storage at e.g. 10° C. or less, for several weeks or months, as described elsewhere herein. The dynamics of the aggregation process are mainly driven by concentration and temperature, which may be determined and utilized according to standard practices in the art.

Immunogenic Compositions

Also provided are pharmaceutically, physiologically acceptable (compatible) immunogenic (antigenic) compositions comprising at least one TSA-1-based recombinant protein or polypeptide as described herein, or optionally, a nucleic acid encoding the protein/polypeptide. Typically, the compositions comprise, as active agent, a therapeutically effective dose of at least one recombinant protein as described herein that is dissolved or dispersed in a pharmaceutically or pharmacologically acceptable carrier.

The phrase "pharmaceutical or pharmacologically acceptable" refers to molecular entities and compositions that do not produce an adverse, allergic or other untoward reaction when administered to an animal, such as, for example, a human. The preparation of a pharmaceutical compositions are known to those of skill in the art as exemplified, for example, by Remington: The Science and Practice of Pharmacy, 21$^{st}$ Ed. Lippincott Williams and Wilkins, 2005, incorporated herein by reference. Moreover, for animal (e.g., human) administration, it will be understood that preparations should meet sterility, pyrogenicity, general safety and purity standards as required by FDA Office of Biological Standards.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, drugs, drug stabilizers, gels, binders, excipients, disintegration agents, lubricants, sweetening agents, flavoring agents, dyes, an such like materials and combinations thereof, as would be known to one of ordinary skill in the art (see, for example, Remington's Pharmaceutical Sciences, 18th Ed. Mack Printing Company, 1990, pp. 1289-1329, incorporated herein by reference). Except insofar as any conventional carrier is incompatible with the active ingredients (e.g. the recombinant proteins described herein), its use in the pharmaceutical compositions is contemplated.

The compositions may comprise different types of carriers depending on whether it is to be administered in solid, liquid or aerosol form, and whether sterilization is required. The compositions can be administered intravenously, intradermally, transdermally, intrathecally, intraarterially, intraperitoneally, intranasally, intravaginally, intrarectally, topically, intramuscularly, subcutaneously, mucosally, orally, topically, locally, inhalation (e.g., aerosol inhalation), injection, infusion, continuous infusion, localized perfusion bathing target cells directly, via a catheter, via a lavage, in creams, in lipid compositions (e.g., liposomes), in a genetically engineered food product, or by other method or any combination of the forgoing as would be known to one of ordinary skill in the art (see, for example, Remington's Pharmaceutical Sciences, 18th Ed. Mack Printing Company, 1990, incorporated herein by reference).

The recombinant proteins may be formulated into a composition in a free base, neutral or pharmaceutically acceptable salt form. Pharmaceutically acceptable salts include the acid addition salts, e.g., those formed with the free amino groups of a proteinaceous composition, or which are formed with inorganic acids such as for example, hydrochloric or phosphoric acids, or such organic acids as acetic, oxalic, tartaric or mandelic acid. Salts formed with the free carboxyl groups can also be derived from inorganic bases such as for example, sodium, potassium, ammonium, calcium or ferric hydroxides; or such organic bases as isopropylamine, trimethylamine, histidine or procaine. Upon formulation, solutions are administered in a manner compatible with the dosage formulation and in such amount as is therapeutically effective. The formulations are easily administered in a variety of dosage forms such as those formulated for parenteral administrations such as injectable solutions, or aerosols for delivery to the lungs, or formulated for alimentary administrations such as drug release capsules and the like.

Further in accordance with the present invention, the compositions of the present invention suitable for administration are typically provided in a pharmaceutically acceptable carrier with or without an inert diluent. The carrier should be assimilable and generally may be or include liquids, semi-solids, i.e., pastes, or solid carriers. Except insofar as any conventional media, agent, diluent or carrier is detrimental to the recipient or to the therapeutic effectiveness of the composition contained therein, its use in administrable composition for use in practicing the methods of the present invention is appropriate. Examples of carriers or diluents include fats, oils, water, saline solutions, lipids, liposomes, resins, binders, fillers and the like, or combinations thereof. The composition may also comprise various antioxidants to retard oxidation of one or more component. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof.

In accordance with the present invention, the composition is combined with the carrier in any convenient and practical manner, i.e., by solution, suspension, emulsification, admixture, encapsulation, absorption and the like. Such procedures are routine for those skilled in the art.

In some aspects, the composition is combined or mixed thoroughly with a semi-solid or solid carrier. The mixing can be carried out in any convenient manner such as grinding, automated blending, etc. Stabilizing agents can be also added in the mixing process in order to protect the composition from loss of therapeutic activity, i.e., denaturation in the stomach. Examples of stabilizers for use in an the composition include buffers, amino acids such as glycine and lysine, carbohydrates such as dextrose, mannose, galactose, fructose, lactose, sucrose, maltose, sorbitol, mannitol, etc.

In further embodiments, the present invention encompasses pharmaceutical lipid vehicle compositions that include one or more types of recombinant proteins, one or more lipids, and an aqueous solvent. As used herein, the term "lipid" includes any of a broad range of substances that is characteristically insoluble in water and extractable with an organic solvent. This broad class of compounds is well known to those of skill in the art, and as the term "lipid" is used herein, it is not limited to any particular structure. Examples include compounds which contain long-chain aliphatic hydrocarbons and their derivatives. A lipid may be naturally occurring or synthetic (i.e., designed or produced by man). However, a lipid is usually a biological substance. Biological lipids are well known in the art, and include for example, neutral fats, phospholipids, phosphoglycerides, steroids, terpenes, lysolipids, glycosphingolipids, glycolipids, sulphatides, lipids with ether and ester-linked fatty acids and polymerizable lipids, and combinations thereof. Of course, compounds other than those specifically described herein that are understood by one of skill in the art as lipids are also encompassed by the compositions and methods of the present invention.

One of ordinary skill in the art would be familiar with the range of techniques that can be employed for dispersing a composition in a lipid vehicle. For example, the recombinant proteins may be dispersed in a solution containing a lipid, dissolved with a lipid, emulsified with a lipid, mixed with a lipid, combined with a lipid, covalently bonded to a lipid, contained as a suspension in a lipid, contained or complexed with a micelle or liposome, or otherwise associated with a lipid or lipid structure by any means known to those of ordinary skill in the art. The dispersion may or may not result in the formation of liposomes.

In general, the pharmaceutical compositions described herein comprise least about 0.1% of an active or agent (i.e. one or more recombinant proteins as described herein). Typically, the compositions comprise from 1-99% recombinant protein(s) by weight. In other embodiments, the an active compound may comprise between about 2% to about 75% of the weight of the unit, or between about 25% to about 60%, for example, and any range derivable therein. Naturally, the amount of active compound(s) in each therapeutically useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable. For example, formulations may vary so that dosages for children are lower than those for adults, etc.

The actual dosage amount of a composition that is administered to an animal patient, which may be a mammal such as a human, is generally determined by physical and physiological factors such as body weight, severity of condition, the type of disease being treated, previous or concurrent therapeutic interventions, age and/or gender of the patient, the route of administration, etc. and is best determined by a skilled professional such as a doctor. Depending upon the dosage and the route of administration, the number of administrations of a preferred dosage and/or an effective amount may vary according to the response of the subject, or upon previously established guidelines, such as a vaccination schedule that includes an initial administration followed by repeated "booster" administrations at predetermined time intervals. The practitioner responsible for administration will, in any event, determine the concentration of active ingredient(s) in a composition and appropriate dose(s) for the individual subject and the appropriate dosing schedule.

In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above.

In certain cases, one or more recombinant proteins is formulated with an immune potentiator or adjuvant. This adjuvant can be, but is not limited to, monophosphoryl lipid A (MPLA), a TLR4 agonist (such as the synthetic TLR4 agonist E6020 (Eisai Co., Ltd)), for example. In addition, the vaccine formulation can be comprised out of one or more delivery vehicles, such as aluminum salts, emulsions, poly (lactic-co-glycolic acid) (PLGA) microspheres, lipidoids, lipoplex, liposome, polymers, carbohydrates (including simple sugars), oligonucleotides, cationic lipids, fibrin gel, fibrin hydrogel, fibrin glue, fibrin sealant, fibrinogen, thrombin, rapidly eliminated lipid nanoparticles and combinations thereof.

In some aspects, compositions comprising the TSA-1-based recombinants disclosed herein also comprise one or more recombinants proteins/polypeptides derived from other *T. cruzi* antigenic proteins, e.g. Tc24-based antigens.

Tc24-Based Antigens

The present disclosure also provides TSA-1-based recombinants in combination with Tc24-based recombinants e.g. in an immunogenic composition for preventing or treating a disease caused by *T. cruzi* infection, such as Chagas disease in humans. The Tc24-based recombinants generally comprise one or more modifications compared to the Tc24 protein found in nature, as described, for example, in International patent application WO2017160849, the complete contents of which are hereby incorporated by reference in entirely. The modification(s) typically concern at least one of four cysteine residues that likely cause intermolecular disulfide bridges and protein aggregation during purification or storage (such as prolonged storage at 2° C. or higher temperatures). In specific aspects, prolonged storage refers to two or more days. Compositions of the disclosure comprising Tc24-based recombinants have storage capability for at least three weeks (for example) compared to storage of a Tc24 protein that lacks the modifications described herein.

Embodiments of the disclosure thus concern certain Tc24 polypeptides and also polynucleotides that express the polypeptides. Specific embodiments provide constructs that encode Tc24 with one or multiple cysteine residues mutated.

In specific embodiments, a particular construct referred to as Tc24-C4, with 4 cysteine residues mutated to serine residues, was genetically engineered and is encompassed herein. Recombinant Tc24-C4, as an example composition, was expressed in *E. coli* (BL21) as soluble protein with similar yields as Tc24, but without any aggregation during purification process. The purified Tc24-C4 did not form any aggregation after being stored at 4° C. for 9 days, as determined by Western blot, light-scattering and HPLC-RP, for example. Vaccine efficacy assays using mouse challenge models showed mice immunized with Tc24-C4 formulated with the immunostimulant E6020-SE (squalene oil-in-water emulsion) were similarly protected as mice immunized with Tc24+E6020-SE, as judged by mouse survival rate and parasitemia levels in blood.

The disclosure concerns non-natural Tc24 polypeptides and their use for a medical purpose. The non-natural Tc24 polypeptides may have any kind of modification compared to wildtype Tc24, but in particular embodiments the modification occurs at least at 1, 2, 3, or all cysteine sites in the naturally occurring polypeptide. In at least some cases, there may be further modifications in addition to the modification(s) at 1, 2, 3, or all cysteine residues. For example, as described elsewhere herein for TSA-1 based recombinants, other amino acid(s) than cysteine may be modified. Other modifications may be made for any purpose, such as to increase immunogenicity, to improve folding, to enhance purification, to increase storage length, to reduce aggregation, and a combination thereof. Examples of modifications include amino acid substitution, deletion, inversion, addition, truncation (C-terminal and/or N-terminal), and so forth. In embodiments wherein amino acid(s) are substituted, the substitution may or may not be conservative. In cases wherein the cysteine residue(s) are substituted, the substitution may or may not be conservative. However, to encourage proper folding, the substitutions at cysteine may be to serine, methionine, or threonine. In a given Tc24 polypeptide, when multiple cysteines are mutated they may or may not be substituted with the same amino acid. All modifications and characteristics thereof that are described for the TSA-1 based recombinants also apply to Tc24-based recombinants, except that the wildtype sequences of course differ.

A nucleotide sequence for Tc24 using an isolate of *T. cruzi* from the Yucatan, Mexico is as follows:

(SEQ ID NO: 6)

```
ATGGGTGCTTGTGGGTCGAAGGGCTCGACGAGCGACAAGG
GGTTGGCGAGCGATAAGGACGGCAAGAACGCCAAGGACCG
CAAGGAAGCGTGGGAGCGCATTCGCCAGGCGATTCCTCGT
GAGAAGACCGCCGAGGCAAAACAGCGCCGCATCGAGCTAT
TCAAGAAGTTCGACAAGAACGAGACTGGGAAGCTGTGCTA
CGATGAGGTGCACAGCGGCTGCCTCGAGGTGCTGAAGTTG
GACGAGTTCACGCCGCGAGTGCGCGACATCACGAAGCGTG
CGTTCGACAAGGCGAGGGCCCTGGGCAGCAAGCTGGAGAA
CAAGGGCTCCGAGGACTTTGTTGAATTTCTGGAGTTCCGT
CTGATGCTGTGCTACATCTACGACTTCTTCGAGCTGACGG
TGATGTTCGACGAGATTGACGCCTCCGGCAACATGCTGGT
CGACGAGGAGGAGCTCAAGCGCGCCGTGCCCAAGCTTGAG
```

-continued

```
GCGTGGGGCGCCAAGGTCGAGGATCCCGCGGCGCTGTTCA
AGGAGCTCGATAAGAATGGCACTGGGTCCGTGACGTTCGA
CGAGTTTGCAGCGTGGGCTTCTGCAGTCAAACTGGACGCC
GACGGCGACCCGGACAACGTGCCGGAGAGCGCG
```

*E. coli* codon optimized DNA sequence for wild type Tc24 (Tc24-WT) is as follows:

(SEQ ID NO: 7)

```
ATGGGTGCTTGTGGCTCCAAAGGTTCAACGAGTGATAAAG
GTCTGGCTTCGGATAAAGATGGTAAAAATGCTAAAGATCG
CAAAGAAGCGTGGGAACGTATTCGCCAGGCCATCCCGCGT
GAAAAAACCGCGGAAGCCAAACAACGTCGCATCGAACTGT
TCAAAAAATTCGATAAAAACGAAACGGGCAAACTGTGCTA
TGACGAAGTGCATAGCGGTTGTCTGGAAGTTCTGAAACTG
GATGAATTCACCCCGCGTGTCCGCGATATCACGAAACGTG
CCTTTGACAAAGCACGCGCTCTGGGCAGCAAACTGGAAAA
CAAAGGTTCTGAAGATTTCGTGGAATTCCTGGAATTTCGT
CTGATGCTGTGCTATATTTACGACTTTTTCGAACTGACCG
TTATGTTCGATGAAATCGACGCAAGCGGCAACATGCTGGT
CGATGAAGAAGAACTGAAACGCGCGGTGCCGAAACTGGAA
GCATGGGGTGCTAAAGTTGAAGATCCGGCGGCCCTGTTTA
AAGAACTGGACAAAAATGGCACCGGTAGTGTTACGTTCGA
TGAATTTGCAGCTTGGGCGTCCGCCGTCAAACTGGATGCA
GACGGCGACCCGGATAATGTCCCGGAATCAGCC
```

Tc24-C4 DNA sequence (*E. coli* codon optimized) is as follows:

(SEQ ID NO: 8)

```
ATGGGTGCTAGCGGCTCCAAAGGTTCAACGAGTGATAAAG
GTCTGGCTTCGGATAAAGATGGTAAAAATGCTAAAGATCG
CAAAGAAGCGTGGGAACGTATTCGCCAGGCCATCCCGCGT
GAAAAAACCGCGGAAGCCAAACAACGTCGCATCGAACTGT
TCAAAAAATTCGATAAAAACGAAACGGGCAAACTGAGCTA
TGACGAAGTGCATAGCGGTAGCCTGGAAGTTCTGAAACTG
GATGAATTCACCCCGCGTGTCCGCGATATCACGAAACGTG
CCTTTGACAAAGCACGCGCTCTGGGCAGCAAACTGGAAAA
CAAAGGTTCTGAAGATTTCGTGGAATTCCTGGAATTTCGT
CTGATGCTGAGCTATATTTACGACTTTTTCGAACTGACCG
TTATGTTCGATGAAATCGACGCAAGCGGCAACATGCTGGT
CGATGAAGAAGAACTGAAACGCGCGGTGCCGAAACTGGAA
```

-continued

```
GCATGGGGTGCTAAAGTTGAAGATCCGGCGGCCCTGTTTA

AAGAACTGGACAAAAATGGCACCGGTAGTGTTACGTTCGA

TGAATTTGCAGCTTGGGCGTCCGCCGTCAAACTGGATGCA

GACGGCGACCCGGATAATGTCCCGGAATCAGCC
```

Codons mutated from cysteine to serine are underlined above.

The Tc24-WT amino acid sequence with the naturally occurring cysteine residues underlined is as follows:

```
                                     (SEQ ID NO: 9)
MGACGSKGST SDKGLASDKD GKNAKDRKEA WERIRQAIPR

EKTAEAKQRR IELFKKFDKNE TGKLCYDEVHSGCLEVLKL

DEFTPRVRDI TKRAFDKARA LGSKLENKGS EDFVEFLEFRLM

LCYIYDFF ELTVMFDEIDASGNMLVDEE ELKRAVPKLE

AWGAKVEDPAALFKELDKNGTGSVT

FDEFAAWASAVKLDADGDPDNVPESA*
```

Tc24-C4 amino acid sequence comprising mutations of all four cysteines:

```
                              (SEQ ID NO: 10)
MGASGSKGST SDKGLASDKD GKNAKDRKEA

WERIRQAIPR EKTAEAKQRR IELFKKFDKN

ETGKLSYDEV HSGSLEVLKL DEFTPRVRDI

TKRAFDKARA LGSKLENKGS EDFVEFLEFR

LM LSYIYDFF ELTVMFDEID ASGNMLVDEE

ELKRAVPKLE AWGAKVEDPA ALFKELDKNG

TGSVTFDEFA AWASAVKLDA DGDPDNVPES A*
```

Amino acids mutated from cysteine to serine are underlined.

In particular embodiments, the immunogenic composition comprises SEQ ID NO: 10 (together with at least one TSA-1 based recombinants). In certain aspects, the immunogenic composition comprises at least one amino acid sequence of SEQ ID NO: 9 except that 1, 2, 3, or all cysteine residues are mutated to another amino acid. In specific aspects, the immunogenic composition comprises modifications compared to SEQ ID NOS: 9 or 10 and is at least 70, 75, 80, 85, 90, 95, 97, 98, or 99% identical to SEQ ID NOS: 9 or 10. The immunogenic composition, in particular aspects, is a fragment of SEQ ID NO: 10 yet still comprises mutation at one or more cysteine residues within the fragment. In specific aspects, the fragment is at least 100, 125, 150, 175, 180, 185, 190, 195, 200, 205, or 210 amino acids in length. In some cases, the fragment is no more than 100, 125, 150, 175, 180, 185, 190, 195, 200, 205, or 210 amino acids in length. The composition may be a fragment of SEQ ID NO: 10 and may also have 1, 2, 3, or 4 cysteines that have been mutated to another amino acid, such as to serine, methionine, or cysteine.

An immunogenic composition of the disclosure is a composition that invokes any kind of immune response to a TSA-1-based antigen in a mammal, including a cell-mediated or humoral response. In some cases, the immunogenic composition may be considered a vaccine. Generally the antigenic composition induces an immune response to the antigen in a cell, tissue or animal (e.g., a human). As used herein, an "antigenic composition" may comprise an antigen (e.g., a peptide or polypeptide), a nucleic acid encoding an antigen (e.g., an antigen expression vector), or a cell expressing or presenting an antigen. In particular embodiments, the antigenic composition comprises or encodes all or part of the sequence shown in SEQ ID NO: 1, or an immunologically functional equivalent thereof (such as a protein that comprises the sequence of SEQ ID NO: 1 but that comprises 1, 2, 3, 4, 5, 6 or more modifications thereto, such as amino acid substitutions, for example). In other embodiments, the antigenic composition is in a mixture that comprises an additional immunostimulatory agent or nucleic acids encoding such an agent. Immunostimulatory agents include but are not limited to, for example, one or more additional antigens (for example, Tc24-based antigens), an immunomodulator, an antigen presenting cell or an adjuvant. In other embodiments, one or more of the additional agent(s) is covalently bonded to the antigen or an immunostimulatory agent, in any combination. In certain embodiments, the antigenic composition is conjugated to or comprises an HLA anchor motif.

An immunogenic composition of the present disclosure may vary in its composition of proteinaceous, nucleic acid and/or cellular components. In a non-limiting example, a nucleic encoding an antigen might also be formulated with a proteinaceous adjuvant. Of course, it will be understood that various compositions described herein may further comprise additional components.

In certain embodiments, an antigenic composition or immunologically functional equivalent may be used as an effective vaccine in inducing an anti-TSA-1 humoral and/or cell-mediated immune response in an animal. The present invention contemplates one or more antigenic compositions or vaccines for use in both active and passive immunization embodiments. An immunogenic composition of the present disclosure, and its various components, may be prepared and/or administered by any method disclosed herein or as would be known to one of ordinary skill in the art, in light of the present disclosure.

Genetic Vaccine Antigens

In certain embodiments, an immune response may be promoted by transfecting or inoculating an animal with a nucleic acid encoding an antigen, such as one encoding a non-natural TSA-1-based antigen of the disclosure. One or more cells comprised within a target animal then expresses the sequences encoded by the nucleic acid after administration of the nucleic acid to the animal. Thus, the vaccine may comprise a "genetic vaccine" useful for immunization protocols. A vaccine may also be in the form, for example, of a nucleic acid (e.g., a cDNA or an RNA) encoding all or part of the peptide or polypeptide sequence of an antigen. Expression in vivo by the nucleic acid may be, for example, by a plasmid type vector, a viral vector, or a viral/plasmid construct vector.

In some aspects, the nucleic acid comprises a coding region that encodes all or part of the sequences disclosed as SEQ ID NO: 1 but with one or more modifications, or an immunologically functional equivalent thereof. In some aspects, SEQ ID NO: 1 and SEQ ID NO: 10 (or a variant thereof) are both encoded by a single nucleic acid. Of course, the nucleic acid may comprise and/or encode additional sequences, including but not limited to those comprising one or more immunomodulators or adjuvants. The nucleotide and protein, polypeptide and peptide encoding sequences for various immunomodulators or adjuvant genes have been previously disclosed, and may be found at computerized databases known to those of ordinary skill in the art. One such database is the National Center for Biotechnology Information's Genbank and GenPept databases (see the website at www.ncbi.nlm.nih.gov/). The coding regions for these known genes may be amplified, combined with the exemplary sequences disclosed herein (e.g., ligated) and/or expressed using the techniques disclosed herein or by any technique that would be known to those of ordinary skill in the art (e.g., Sambrook et al., 1987). Though a nucleic acid may be expressed in an in vitro expression system, in some embodiments the nucleic acid comprises a vector for in vivo replication and/or expression.

Cellular Vaccine Antigens

In another embodiment, a cell expressing at least one of the TSA-1-based antigens of the disclosure may be present in the immunogenic composition (such as a vaccine). The cell may be isolated from a culture, tissue, organ or organism and administered to an animal as a cellular immunogenic composition (such as a cellular vaccine). Thus, the present disclosure contemplates a "cellular vaccine." The cell may be transfected with a nucleic acid encoding an antigen to enhance its expression of the antigen. Of course, the cell may also express one or more additional vaccine components, such as immunomodulators or adjuvants. A vaccine may comprise all or part of the cell.

In particular embodiments, it is contemplated that nucleic acids encoding antigens of the present invention may be transfected into plants, particularly edible plants, and all or part of the plant material used to prepare a vaccine, such as for example, an oral vaccine. Such methods are described in U.S. Pat. Nos. 5,484,719, 5,612,487, 5,914,123, 5,977,438 and 6,034,298, each incorporated herein by reference.

Alimentary Compositions and Formulations

In some aspects of the present invention, the compositions are formulated to be administered via an alimentary route. Alimentary routes include all possible routes of administration in which the composition is in direct contact with the alimentary tract. Specifically, the pharmaceutical compositions disclosed herein may be administered orally, buccally, rectally, or sublingually. As such, these compositions may be formulated with an inert diluent or with an assimilable edible carrier, or they may be enclosed in hard- or soft-shell gelatin capsule, or they may be compressed into tablets, or they may be incorporated directly into a food of the diet.

The active agents may be incorporated with excipients and used in the form of ingestible tablets, buccal tables, troches, capsules, elixirs, suspensions, syrups, wafers, and the like (Mathiowitz et al., 1997; Hwang et al., 1998; U.S. Pat. Nos. 5,641,515; 5,580,579 and 5,792, 451, each specifically incorporated herein by reference in its entirety). The tablets, troches, pills, capsules and the like may also contain the following: a binder, such as, for example, gum tragacanth, acacia, cornstarch, gelatin or combinations thereof; an excipient, such as, for example, dicalcium phosphate, mannitol, lactose, starch, magnesium stearate, sodium saccharine, cellulose, magnesium carbonate or combinations thereof; a disintegrating agent, such as, for example, corn starch, potato starch, alginic acid or combinations thereof; a lubricant, such as, for example, magnesium stearate; a sweetening agent, such as, for example, sucrose, lactose, saccharin or combinations thereof; a flavoring agent, such as, for example peppermint, oil of wintergreen, cherry flavoring, orange flavoring, etc. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar, or both. When the dosage form is a capsule, it may contain, in addition to materials of the above type, carriers such as a liquid carrier. Gelatin capsules, tablets, or pills may be enterically coated. Enteric coatings prevent denaturation of the composition in the stomach or upper bowel where the pH is acidic. See, e.g., U.S. Pat. No. 5,629,001. Upon reaching the small intestines, the basic pH therein dissolves the coating and permits the composition to be released and absorbed by specialized cells, e.g., epithelial enterocytes and Peyer's patch M cells. A syrup of elixir may contain the active compound sucrose as a sweetening agent methyl and propylparabens as preservatives, a dye and flavoring, such as cherry or orange flavor. Of course, any material used in preparing any dosage unit form should be pharmaceutically pure and substantially non-toxic in the amounts employed. In addition, the active compounds may be incorporated into sustained-release preparation and formulations.

For oral administration the compositions of the present invention may alternatively be incorporated with one or more excipients in the form of a mouthwash, dentifrice, buccal tablet, oral spray, or sublingual orally-administered formulation. For example, a mouthwash may be prepared incorporating the active ingredient in the required amount in an appropriate solvent, such as a sodium borate solution (Dobell's Solution). Alternatively, the active ingredient may be incorporated into an oral solution such as one containing sodium borate, glycerin and potassium bicarbonate, or dispersed in a dentifrice, or added in a therapeutically-effective amount to a composition that may include water, binders, abrasives, flavoring agents, foaming agents, and humectants. Alternatively the compositions may be fashioned into a tablet or solution form that may be placed under the tongue or otherwise dissolved in the mouth.

Additional formulations which are suitable for other modes of alimentary administration include suppositories. Suppositories are solid dosage forms of various weights and shapes, usually medicated, for insertion into the rectum. After insertion, suppositories soften, melt or dissolve in the cavity fluids. In general, for suppositories, traditional carriers may include, for example, polyalkylene glycols, triglycerides or combinations thereof. In certain embodiments, suppositories may be formed from mixtures containing, for example, the active ingredient in the range of about 0.5% to about 10%, and preferably about 1% to about 2%.

Parenteral Compositions and Formulations

In further embodiments, the compositions may be administered via a parenteral route. As used herein, the term "parenteral" includes routes that bypass the alimentary tract. Specifically, the pharmaceutical compositions disclosed herein may be administered for example, but not limited to intravenously, intradermally, intramuscularly, intraarterially, intrathecally, subcutaneous, or intraperitoneally U.S. Pat. Nos. 6,7537,514, 6,613,308, 5,466,468, 5,543,158; 5,641, 515; and 5,399,363 (each specifically incorporated herein by reference in its entirety).

Solutions of the active compounds as free base or pharmacologically acceptable salts may be prepared in water suitably mixed with a surfactant, such as hydroxypropylcellulose. Dispersions may also be prepared in glycerol, liquid polyethylene glycols, and mixtures thereof and in oils. Under ordinary conditions of storage and use, these preparations contain a preservative to prevent the growth of microorganisms. The pharmaceutical forms suitable for injectable use include sterile aqueous solutions or dispersions and sterile powders for the extemporaneous preparation of sterile injectable solutions or dispersions (U.S. Pat. No. 5,466,468, specifically incorporated herein by reference in its entirety). In all cases the form must be sterile and must be fluid to the extent that easy injectability exists. It must be stable under the conditions of manufacture and storage and must be preserved against the contaminating action of microorganisms, such as bacteria and fungi. The carrier can be a solvent or dispersion medium containing, for example, water, ethanol, polyol (i.e., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous, and intraperitoneal administration. In this connection, sterile aqueous media that can be employed will be known to those of skill in the art in light of the present disclosure. For example, one dosage may be dissolved in isotonic NaCl solution and either added hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof. A powdered composition is combined with a liquid carrier such as, e.g., water or a saline solution, with or without a stabilizing agent.

Miscellaneous Pharmaceutical Compositions and Formulations

In other aspects of the invention, the compositions may be formulated for administration via various miscellaneous routes, for example, topical (i.e., transdermal) administration, mucosal administration (intranasal, vaginal, etc.) and/or inhalation.

Pharmaceutical compositions for topical administration may include the active compound formulated for a medicated application such as an ointment, paste, cream or powder. Ointments include all oleaginous, adsorption, emulsion and water-soluble based compositions for topical application, while creams and lotions are those compositions that include an emulsion base only. Topically administered medications may contain a penetration enhancer to facilitate adsorption of the active ingredients through the skin. Suitable penetration enhancers include glycerin, alcohols, alkyl methyl sulfoxides, pyrrolidones and laurocapram. Possible bases for compositions for topical application include polyethylene glycol, lanolin, cold cream and petrolatum as well as any other suitable absorption, emulsion or water-soluble ointment base. Topical preparations may also include emulsifiers, gelling agents, and antimicrobial preservatives as necessary to preserve the active ingredient and provide for a homogenous mixture. Transdermal administration of the present invention may also comprise the use of a "patch". For example, the patch may supply one or more active substances at a predetermined rate and in a continuous manner over a fixed period of time.

In certain embodiments, the pharmaceutical compositions may be delivered by eye drops, intranasal sprays, inhalation, and/or other aerosol delivery vehicles. Methods for delivering compositions directly to the lungs via nasal aerosol sprays has been described e.g., in U.S. Pat. Nos. 5,756,353 and 5,804,212 (each specifically incorporated herein by reference in its entirety). Likewise, the delivery of drugs using intranasal microparticle resins (Takenaga et al., 1998) and lysophosphatidyl-glycerol compounds (U.S. Pat. No. 5,725,871, specifically incorporated herein by reference in its entirety) are also well-known in the pharmaceutical arts. Likewise, transmucosal drug delivery in the form of a polytetrafluoroetheylene support matrix is described in U.S. Pat. No. 5,780,045 (specifically incorporated herein by reference in its entirety).

The term aerosol refers to a colloidal system of finely divided solid of liquid particles dispersed in a liquefied or pressurized gas propellant. The typical aerosol of the present invention for inhalation will consist of a suspension of active ingredients in liquid propellant or a mixture of liquid propellant and a suitable solvent. Suitable propellants include hydrocarbons and hydrocarbon ethers. Suitable containers will vary according to the pressure requirements of the propellant. Administration of the aerosol will vary according to subject's age, weight and the severity and response of the symptoms.

Methods of Prevention and Treatment

Diagnosis

In some aspect, the treatment methods described herein include a step of identifying subjects suitable for treatment with the disclosed recombinants. In a typical case of Chagas disease, the symptoms change over the duration of the infection. For example, in the beginning stages, the individual is asymptomatic or the symptoms are mild, including, for example, fever, swollen lymph nodes, headaches, and/or localized swelling at the location of the initial bite. After approximately 8-12 weeks, there is onset of the chronic phase of the disease, which may or may not produce further symptoms. However, for some—approximately 25-33% of patients—there are additional symptoms even 10 to 30 years after the initial infection. Such symptoms include but are not limited to damage to and fibrosis of the heart myocardial tissue, arrhythmias and disturbance of the heart electrical conduction system that can result in sudden cardiac death, enlargement of the ventricles of the heart (which may lead to heart failure); an enlarged esophagus; an enlarged colon, neuronal cell loss, microvascular dysfunction, and/or myocardial damage.

Diagnosis of early disease may occur by microscopic analysis for the pathogen, while chronic disease may be diagnosed using assays of blood samples for antibodies for *T. cruzi*, for example. Another way to diagnose is by using polymerase chain reaction (PCR) to detect *T. cruzi* DNA. In certain embodiments, methods of the disclosure encompass methods of determining that an individual has Chagas disease or has been exposed to or is infected with *T. cruzi*.

Prevention and Treatment

Methods of the disclosure include those for treatment and/or prevention of a medical condition caused directly or indirectly by *T. cruzi*, such as Chagas disease. The methods generally involve administering a therapeutically effective amount of at least one recombinant protein as described herein, generally in a pharmaceutically acceptable composition, to a subject in need thereof. Generally, an effective amount of one or more recombinant proteins is an amount sufficient to invoke an immune response. The immune response may be of any kind, including cellular and humoral immune responses.

Although the methods may be for any purpose, in some aspects the methods are for a therapeutic purpose, including treatment and/or prevention of a certain medical condition associated with trypanosomes including at least *T. cruzi*. In general, methods of "treating" are begun after a subject has contracted a disease, or at least after a subject is suspected of having been exposed to the etiological agent of the disease (e.g. the subject has been bitten by a triatomine insect vector, has received a blood transfusion that may contain *T. cruzi*, etc.), and may be commenced after a subject exhibits one or more disease-related symptoms, and/or after a subject has been definitively diagnosed as infected with *T. cruzi*, with or without overt disease symptoms.

In prevention methods, administration of the recombinant may occur prophylactically prior to exposure to *T. cruzi*, in which case infection may be prevented. However, "prevention" may also include administration after infection (e.g. after a bite) but prior to onset of one or more symptoms in order to prevent the manifestation of those symptoms, e.g. after early (acute) symptoms but before (or when) later, chronic symptoms of infection occur. Thus, the development of one or more symptoms of acute infection or chronic infection may be prevented. Whenever administered, the treatments result at least in amelioration, and sometimes complete alleviation, reversal or prevention, of at least one symptom of the disease and/or in a reduction in severity of and/or a delay in onset of at least one symptom of the disease. The outcome of the treatment may occur at any time following the treatment, including within days, weeks, months, or years of the treatment.

In some aspects, the medical condition that is treated or prevented is Chagas disease in humans. The acute phase of Chagas disease, which lasts for weeks or months, is often symptom-free. When signs and symptoms do occur, they are usually mild and may include: swelling and/or redness at the infection site (termed chagoma), fever, fatigue, rash, head and body aches, eyelid swelling, headache, loss of appetite, nausea, vomiting and/or diarrhea, swollen glands (e.g. swollen lymph nodes), and enlargement of the liver or spleen. While signs and symptoms that develop during the acute phase may resolve on their own, if left untreated, the infection persists and, in some cases, advances to the chronic phase. Signs and symptoms of the chronic phase of Chagas disease may occur up to e.g. even 10 to 20 years after initial infection. Chronic Chagas disease signs and symptoms may include: irregular heartbeat, EKG changes, palpitations, fainting (syncope), cardiomyopathy, congestive heart failure, sudden cardiac arrest, shortness of breath (dyspnea), emphysema, stroke, difficulty swallowing due to an enlarged esophagus, and/or abdominal pain or constipation due to enlarged colon.

In some aspects, what is treated or prevented by administration of the recombinants disclosed herein is heart damage and/or a symptom of heart damage. For example, as demonstrated in the Examples section below, when TSA-1-C4 was administered with the Tc24-based recombinant Tc24-C4, the number of parasites in the blood and the number of inflammatory cells in the heart of infected subjects were both dramatically reduced.

Subjects that are treated as described herein may be treated at any stage of disease e.g. prior to or after symptoms of acute or chronic infection are detected, or prior to infection. Subjects suitable for treatment may reside in any region of the world or travel to any region of the world. In some aspects, the subjects reside in and/or travel to North America, Central America, or South America. The individual being treated may be known to have Chagas disease, may be suspected of having Chagas disease, may be traveling to or may have traveled to a region of the world that puts the individual at risk for Chagas disease, may have been exposed to *T. cruzi*, may have been suspected of having been exposed to *T. cruzi*, may be in need of routine prevention of Chagas disease, may be seropositive for *T. cruzi*, may be in the military or in a vocation that requires travel, and so forth.

In some aspects, methods of treatment and/or prevention include administration of another agent in addition to (in combination with, or together with) the administration of a composition(s) of the disclosure. For example, early infections are often treated with benznidazole or nifurtimox and may be combined with the recombinants. While these two drugs apparently work best for treating the early acute stages of the infection, their use for treating chronic infections is not excluded, especially when combined with the recombinants described herein. For individuals with chronic disease, these medications may delay or prevent the development of end-stage symptoms. When one or more agents other than the recombinants of the disclosure are provided to an individual, the administrations may occur at the same time or at separate times. When given at the same time, the active agents that are administered may or may not be administered to the individual by the same administration route, and may be administered as a single composition or as separate compositions. When given at separate times, they may or may not be administered to the individual by the same administration route. When given at separate times, the duration of time between delivery of the separate agents may be of any duration, including of minutes, hours, days, months, or years.

In addition, subjects with late stage Chagas symptoms involving the heart may receive other standard heart medications, e.g. angiotensin-converting enzyme (ACE) inhibitors, angiotensin II receptor blockers, beta blockers, diuretics, aldosterone antagonists, inotropes, digoxin, etc. in a treatment protocol that includes the disclosed recombinant proteins.

Vaccine Protocols

The treatment methods may be provided to the individual in need thereof only once (e.g. a single administration) or multiple times, e.g. via multiple administrations, e.g.

"booster" doses may be administered. Separate administrations may be separated in time by minutes, days, hours, weeks, months, or years.

Kits

Any of the compositions described herein may be comprised in a kit. In a non-limiting example, a recombinant protein, such as one comprising one or more fewer cysteine residues compared to wild type, is comprised in a kit, and in specific embodiments, a carrier and/or an additional agent, may be comprised in a kit.

The components of the kits may be packaged either in aqueous media or in lyophilized form. The container means of the kits will generally include at least one vial, test tube, flask, bottle, syringe or other container means, into which a component may be placed, and preferably, suitably aliquoted. Where there are more than one component in the kit, the kit also will generally contain a second, third or other additional container into which the additional components may be separately placed. However, various combinations of components may be comprised in a vial. The kits of the present invention also will typically include a means for containing the recombinant protein and any other reagent containers in close confinement for commercial sale. Such containers may include injection or blow-molded plastic containers in which the desired vials are retained.

When the components of the kit are provided in one and/or more liquid solutions, the liquid solution is generally an aqueous solution, with a sterile aqueous solution being particularly preferred. The recombinant protein compositions may also be formulated into a syringeable composition, in which case, the container may itself be a syringe, pipette, and/or other such like apparatus, from which the formulation may be applied to an infected area of the body, injected into an animal, and/or even applied to and/or mixed with the other components of the kit. However, the components of the kit may be provided as dried (e.g. lyophilized) powder(s). When reagents and/or components are provided as a dry powder, the powder can be reconstituted by the addition of a suitable solvent. It is envisioned that the solvent may also be provided in the kit.

Irrespective of the number and/or type of containers, the kits of the invention may also comprise, and/or be packaged with, an instrument for assisting with the injection/administration and/or placement of the recombinant protein within the body of an animal. Such an instrument may be a syringe, pipette, forceps, and/or any such medically approved delivery vehicle.

In the description of the invention herein, it is understood that a word appearing in the singular encompasses its plural counterpart, and a word appearing in the plural encompasses its singular counterpart, unless implicitly or explicitly understood or stated otherwise. Furthermore, it is understood that for any given component or embodiment described herein, any of the possible candidates or alternatives listed for that component may generally be used individually or in combination with one another, unless implicitly or explicitly understood or stated otherwise. Moreover, it is to be appreciated that the figures, as shown herein, are not necessarily drawn to scale, wherein some of the elements may be drawn merely for clarity of the invention. Also, reference numerals may be repeated among the various figures to show corresponding or analogous elements. Additionally, it will be understood that any list of such candidates or alternatives is merely illustrative, not limiting, unless implicitly or explicitly understood or stated otherwise. In addition, unless otherwise indicated, numbers expressing quantities of ingredients, constituents, reaction conditions and so forth used in the specification and claims are to be understood as being modified by the term "about."

Accordingly, unless indicated to the contrary, the numerical parameters set forth in the specification and attached claims are approximations that may vary depending upon the desired properties sought to be obtained by the subject matter presented herein. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the subject matter presented herein are approximations, the numerical values set forth in the specific examples are reported as precisely as possible. Any numerical values, however, inherently contain certain errors necessarily resulting from the standard deviation found in their respective testing measurements.

All patents and publications mentioned in the specification are indicative of the level of those skilled in the art to which the invention pertains. All patents and publications are herein incorporated by reference in their entirety to the same extent as if each individual publication was specifically and individually indicated to be incorporated by reference.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLES

Example 1. Preparation of Soluble Antigen

Figure 3B:
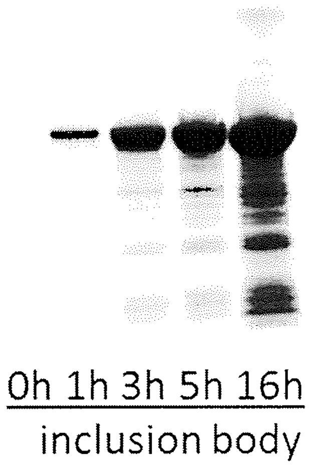
Figure 4A:
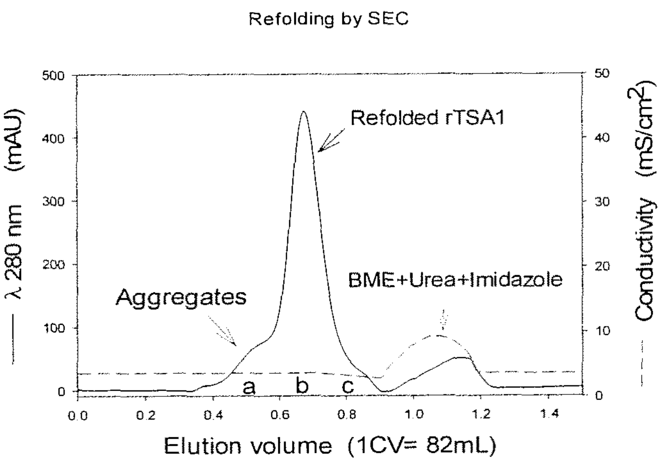
FIGS. 4A-C. On-column refolding of TSA-1-NT. A, chromatographic profile of TSA-1-NT refolded by Size Exclusion Chromatography; B, samples were collected and analyzed by SDS-PAGE under non-reducing condition aggregates (a), and refolded protein (b and c); C, refolded TSA1-NT (b) after one month at 4° C. under reducing (lanes 1,3) and non-reducing conditions (lane 2).
Figure 4B:
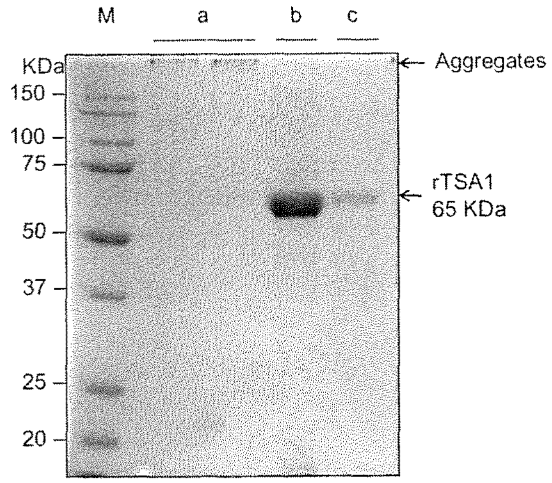
Figure 4C:
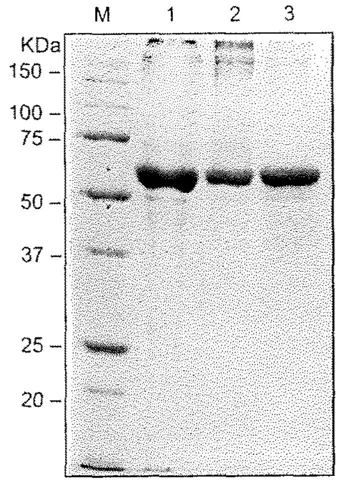

In order to develop as a recombinant protein vaccine that can be used in humans in endemic areas, the coding DNA for TSA-1-NT was identified and codon optimized for expression in *E. coli.* The synthesized DNA was cloned into pET41a, a bacterial expression vector with an IPTG inducible T7 promoter. The recombinant TSA-1-NT/pET41a plasmid DNA was transformed into *E. coli* BL21 (DE3). The recombinant TSA-1-NT was highly expressed upon induction with 0.5 mM IPTG in the insoluble fraction, indicating rTSA-1-NT was expressed as insoluble protein in inclusion body (FIGS. 3A and B). However, the recombinant TSA-1-NT was soluble in 8M urea. The urea-denatured rTSA1-NT could be refolded on a size exclusion column with gradually reduced urea concentrations (FIGS. 4A, 4B). The on-column refolded TSA-1-NT was soluble but aggregated when stored at 4° C. one month (FIG. 4C). Aggregation causes problems with reproducibility and consistency, and would prevent the protein from being developed into a vaccine formulation. We hypothesized that the reason for the aggregation was the interaction of four cysteine residues in the sequence of the molecule (C248, C267, C360, C447) that could lead to intermolecular disulfide bridges.

In order to eliminate the intramolecular aggregation caused by the disulfide bridges in the original TSA-1-NT, a new construct, TSA-1-C4, with the four cysteine residues mutated to serine residues (C248S, C267S, C360S, C447S), and with an additional 43 amino acids at the C-terminus (EFSHFYFGGDEGDSGSDATLTDVFLYNRPLSVGELK-MIKEVED (SEQ ID NO: 4; residues 618-660 of TSA-1 of *T. cruzi*) was genetically engineered (SEQ ID NO: 3 in FIG. 2). The reason for using serine residues to replace the cysteine residues was their similar size. The 43 aa fragment was identified after analysis of a 3D model of TSA-1 obtained using the I_tasser server (Iterative Threading ASSEmbly Refinement, zhanglab.ccmb.med.umich.edu/I-TASSER/), and the template of the *Trypanosoma rangeli* sialidase (PDB 2AGS). That analysis suggested that 43 aa (residues 618-660 of TSA-1) could be advantageously added to complete a 2nd protein domain.

Figures 6A, 6B:
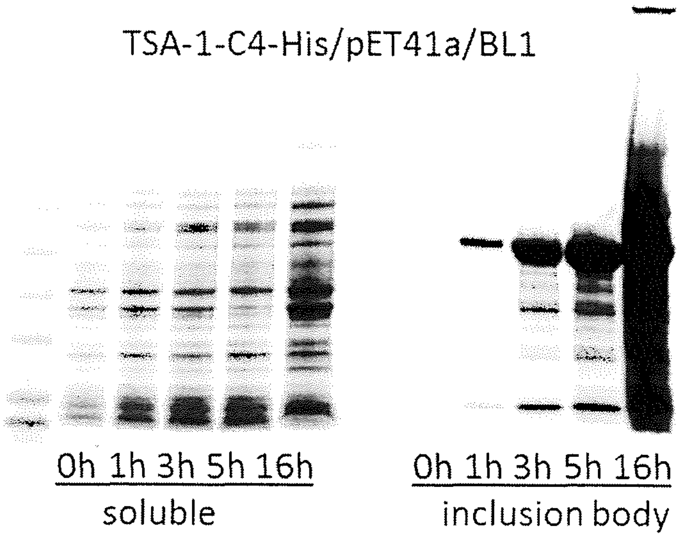
FIGS. 6A and B. SDS-PAGE of expressed TSA-1-C4 in *E. coli* BL21 (DE3) induced with 0.5 mM IPTG over 16 hours. A, soluble protein; B, inclusion body staining.
Figure 7A:
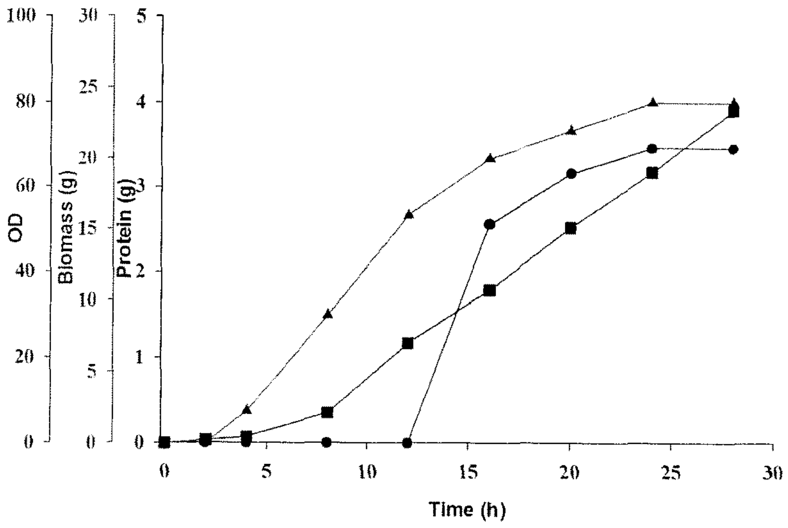
FIGS. 7A, B and C. Production of TSA-1 C4 in a 10 L fermenter. A, fermentation profile; Optical Density (OD-triangles), biomass (g Dry Weight), expressed protein (g/L of culture-circles). B, SDS-PAGE of samples normalized at 1 OD; C, TSA-1 C4 solubilized from inclusion bodies.
Figure 7B:
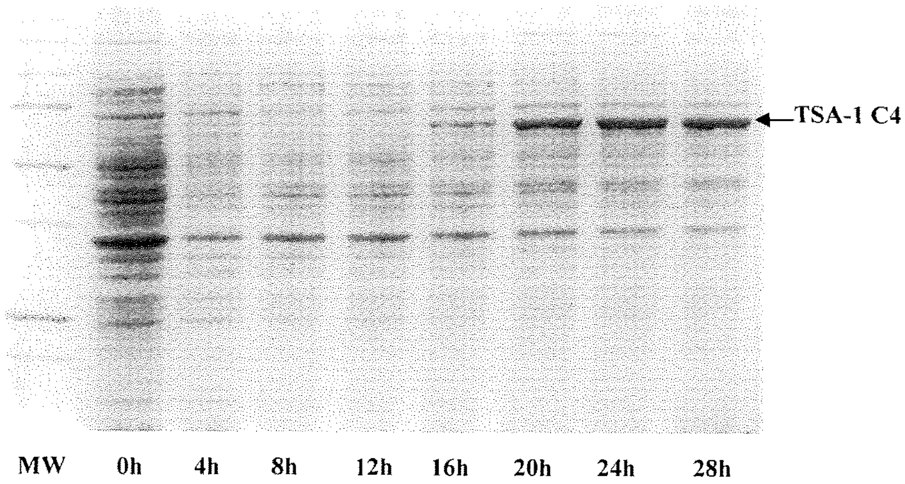
Figure 7C:
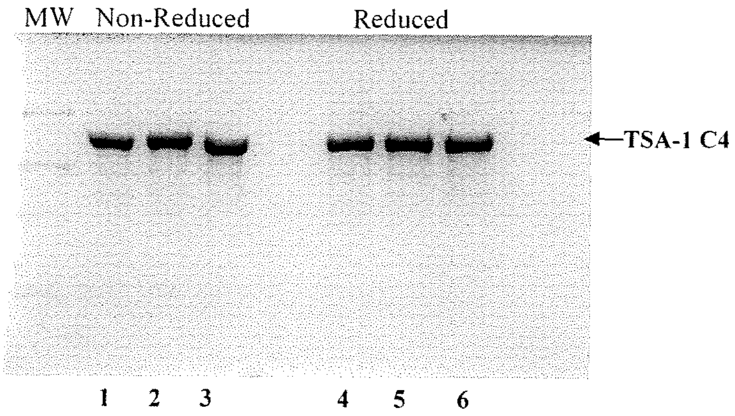

The coding DNA for TSA-1-C4 (SEQ ID NO: 5) was codon optimized for expression in *E. coli*, synthesized by GenScript, and cloned into pET41a with an octahistidine-tag (SEQ ID NO: 11, HHHHHHHH, shaded in FIG. 5A) or without an octahistidine-tag (SEQ ID NO: 3, FIG. 2 and FIG. 5B) expressed at its C-terminus. The recombinant plasmid DNAs were transformed into *E. coli* BL21 (DE3) and selected on LB agar plates containing 30 μg/mL of kanamycin. The correct sequences and reading frames were confirmed by double-strand DNA sequencing with vector flanking primers. After being induced with 0.5 mM IPTG, TSA1-C4 had an expression yield similar or higher to that of TSA-1-NT. Like TSA-1-NT, TSA-1-C4 was expressed as insoluble protein in inclusion bodies (FIGS. 6A and B) but was soluble in 8M urea. The production of TSA-1 C4 with or without the Histidine tag was significantly improved using a high-cell density fermentation culture (FIGS. 7A, B, C).

Figure 8A:
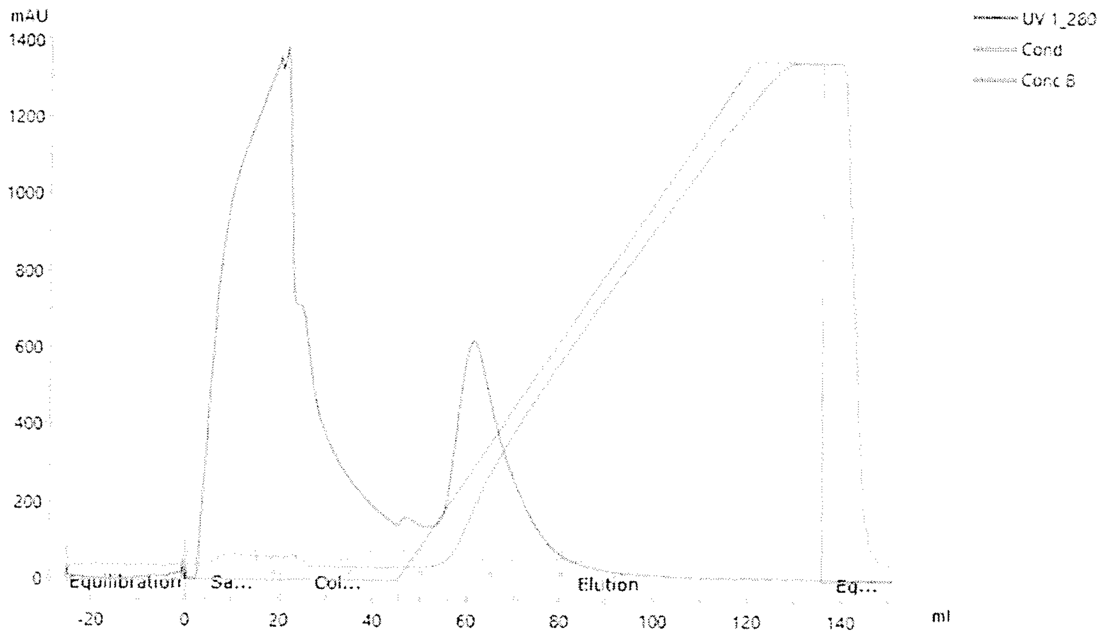
FIGS. 8A and B. Purification of denatured TSA-1-C4. A, Chromatographic profile of TSA-1 C4 purification by Ion-Exchange chromatography. B, SDS-PAGE analysis of collected fractions; unpurified and denatured TSA-1 C4 (lane 2), flow-through and column wash (lanes 3 to 7), and elution (lane 8 to 15).
Figure 8B:
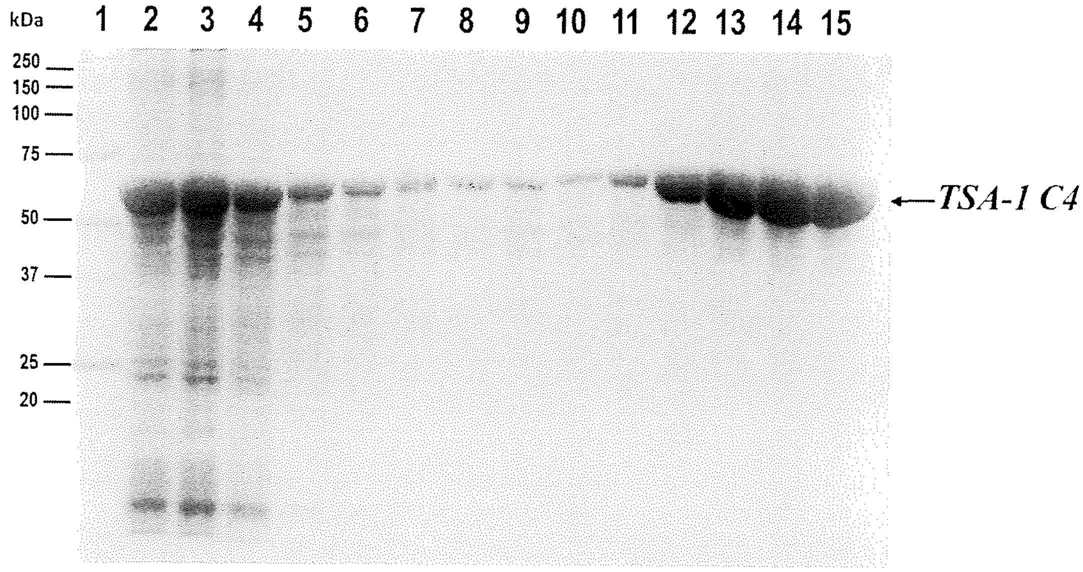
Figure 9A:
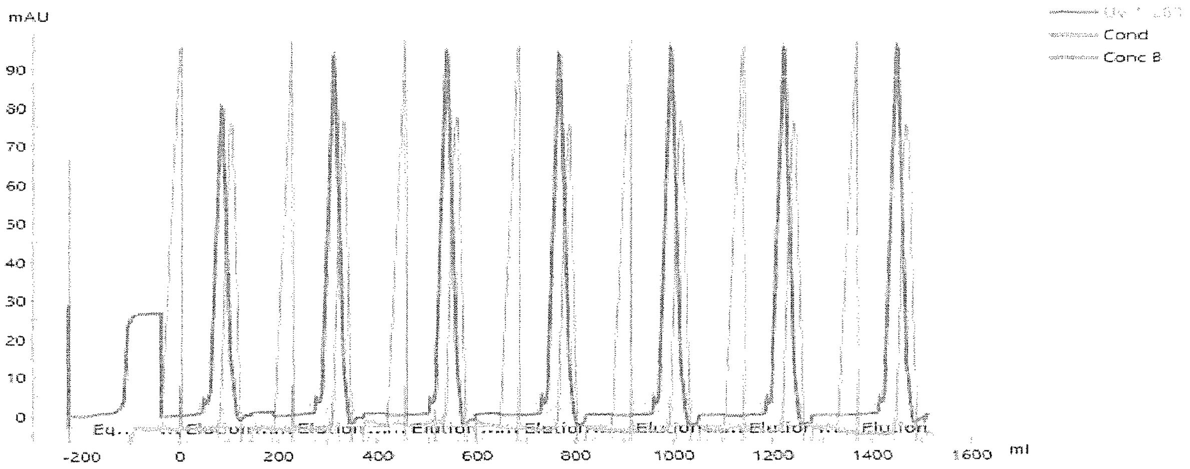
FIGS. 9A and B. Refolding of TSA-1 C4 by Size Exclusion Chromatography (SEC). A, Chromatographic profile of seven consecutive refolding batches of denatured TSA-1 C4 in a 1.6×100 XK column packed with 185 ml of Sepharose 6FF. B, Chromatographic profile of one refolding batch of TSA-1 C4; fractions of refolded protein (main peak of blue line) were collected and analyzed by SDS-PAGE.
Figure 9B:
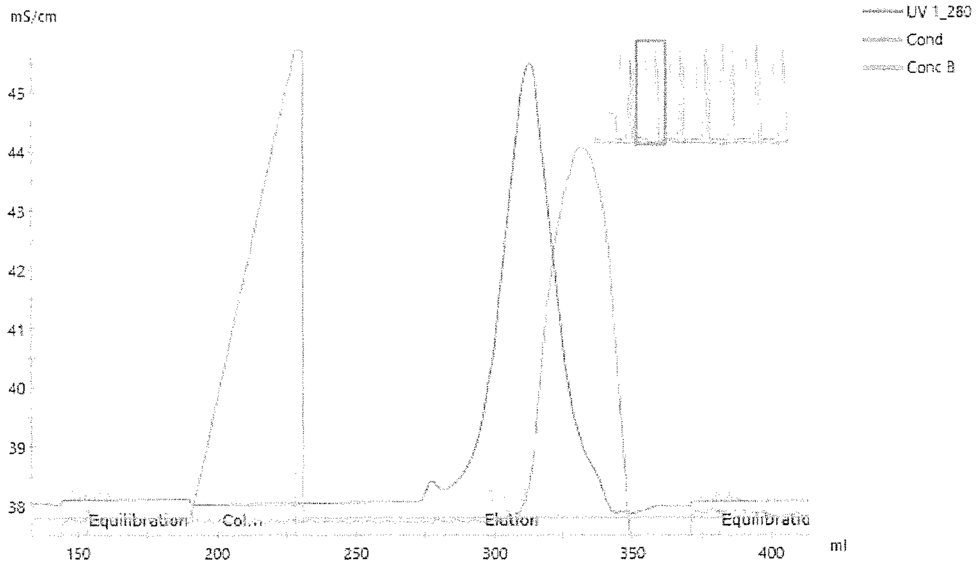
Figure 10A:
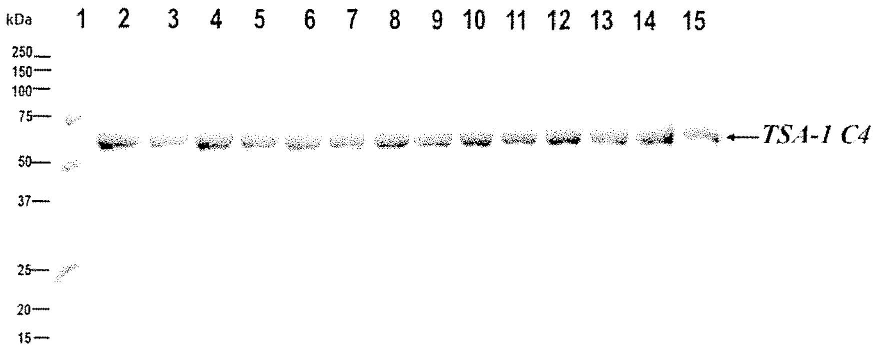
FIGS. 10A, B and C. SDS-PAGE analysis of refolded TSA-1 C4 by Size-Exclusion Chromatography. A, the collected fractions of the main peak of seven consecutive refolding batches of denatured TSA-1 C4 (in 1.6×100 XK column packed with 185 ml of Sepharose 6FF) were analyzed by 10% SDS-PAGE under non-reducing conditions; batch 1 (Lanes 2 and 3), batch 2 (Lanes 4 and 5), batch 3 (Lanes 6 and 7), batch 4 (Lanes 8 and 9), batch 5 (Lanes 10 and 11), batch 6 (Lanes 12 and 13), batch 7 (Lanes 14 and 15). B, Refolded TSA-1-C4 was stored at 4° C. in refolding buffer (lanes 1,4), Tris-HCl (lanes 2 and 5) and PBS (lanes 3 and 6) buffers. Samples were analyzed by SDS-PAGE under non-reduced conditions before (lanes 1, 2 and 3) and after one month (lanes 4, 5 and 6) of storage at 4° C. C, the stability of refolded TSA-1-C4 was tested by orbital stirring at 25 rpm and 20° C. for 24 (lane 2), 48 (lane 3) and 120 h (lane 4), and by cycles of freezing (−80° C.)-thawing at 24 h (lane 5), 48 (lane 6) and (lane 7). Molecular Weight marker (lane 1).
Figure 10B:
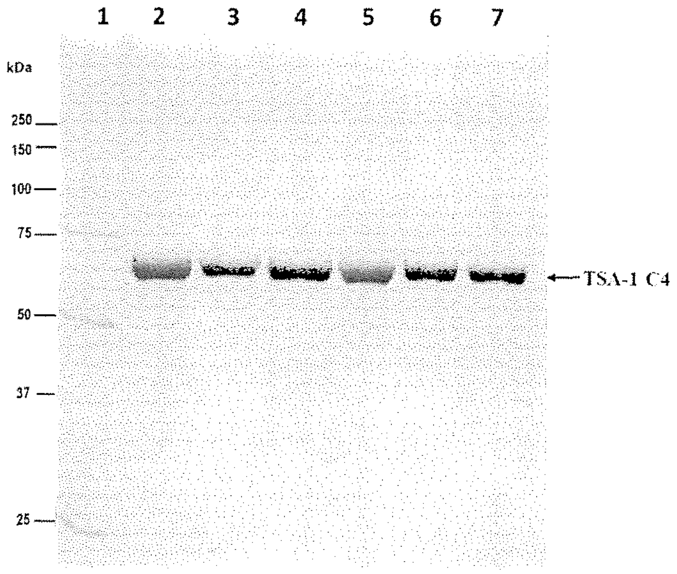
Figure 10C:
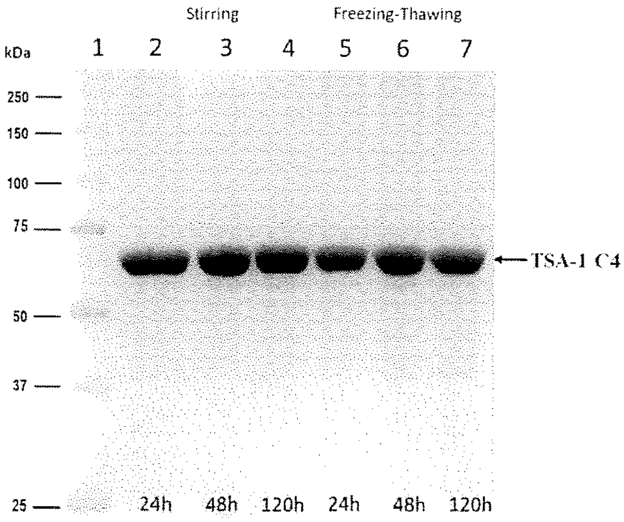

However, and more importantly, and unlike TSA-1 NT, after purification on a nickel column or ion-exchange chromatography (FIGS. 8A and B) and refolding on a size-exclusion column (FIGS. 9A and B). The refoldedTSA-1-C4 was concentrated by ultrafiltration, analyzed by SDS-PAGE (FIG. 10A) and it was stable. No aggregation observed with on-column refolded TSA-1-C4 when stored at 4° C. for one month, in PBS as determined by visual analysis as well as SDS-PAGE (FIG. 10B) or Western blot (not shown), as well as, after 120 h under stirring and cycles of freezing-thawing at 24, 48 and 120h (FIG. 10C).

Example 2. Vaccine Efficacy Testing Using Mouse Challenge Models

Vaccine efficacy testing was performed as shown in Table 1.

TABLE 1

| Group Label | Group Size | Antigen or Control | Antigen Dose (μg) | Adjuvant | Adjuvant | Route of Administration |
|---|---|---|---|---|---|---|
| 1 | 10 | Saline | | — | — | IM |
| 2 | 10 | Benznidazole | 25 mg/kg/day | — | — | Oral |
| 3 | 10 | Tc24-C4 | 20 | — | — | IM |
| 4 | 10 | TSA-1-C4 | 20 | — | — | IM |
| 5 | 10 | Tc24-C4 + MPLA | 20 | MPLA | 10 | IM |
| 6 | 10 | TSA-1-C4 + MPLA | 20 | MPLA | 10 | IM |
| 7 | 10 | Tc24-C4 + TSA-1-C4 + MPLA | 20 each | MPLA | 10 | IM |
| 8 | 10 | Benznidazole + Tc24-C4 + TSA-1-C4 + MPLA | 25 mg/kg/day | MPLA | 10 | Oral/IM |
| 9 | 10 | — | — | MPLA | 10 | IM |

Figure 11A:
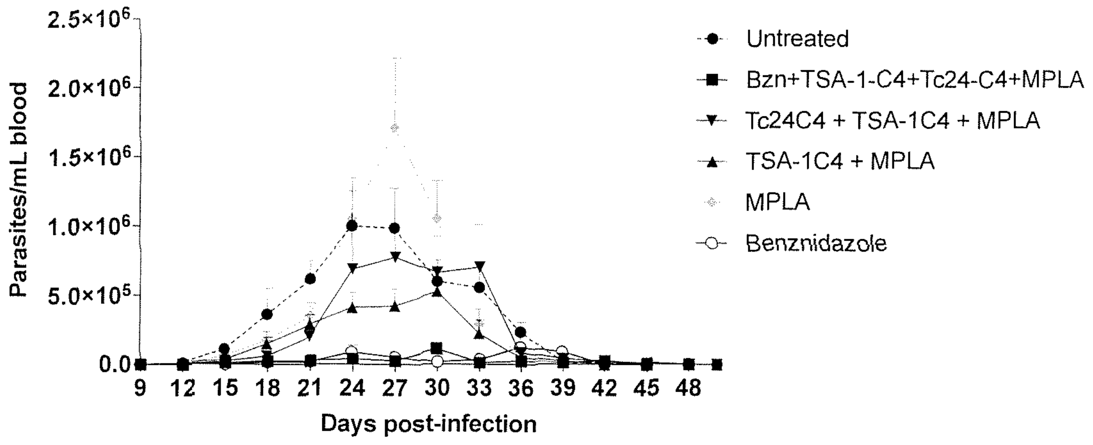
FIGS. 11A and B. Therapeutic effect of TSA-1-C4 alone or with Tc24-C4 and in a combination with or without benznidazole (BZN) treatment. H1 *Trypanosoma cruzi*-infected mice were treated with Tc24-C4 and TSA-1-C4, 20 ug each and given orally 25 mg/kg BZN per day for 20 days. A, Kinetic parasitemia was recorded each 3 days during the acute infection. Standard bars represent the error of the mean. B, Area under the curve (AUC) was graphed using the simple method of Gagnon. Histograms represent the mean and standard bars the error of the mean. (*) Statistically significant differences were observed with a P value <0.05.
Figure 11B:
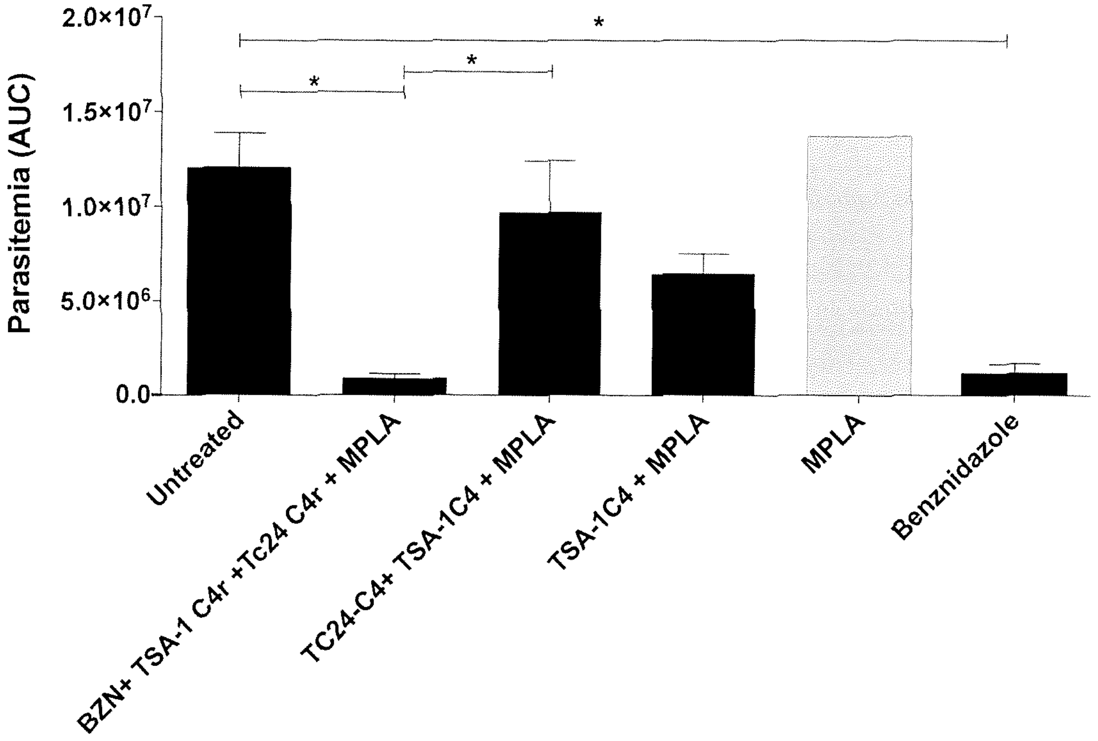
Figure 12:
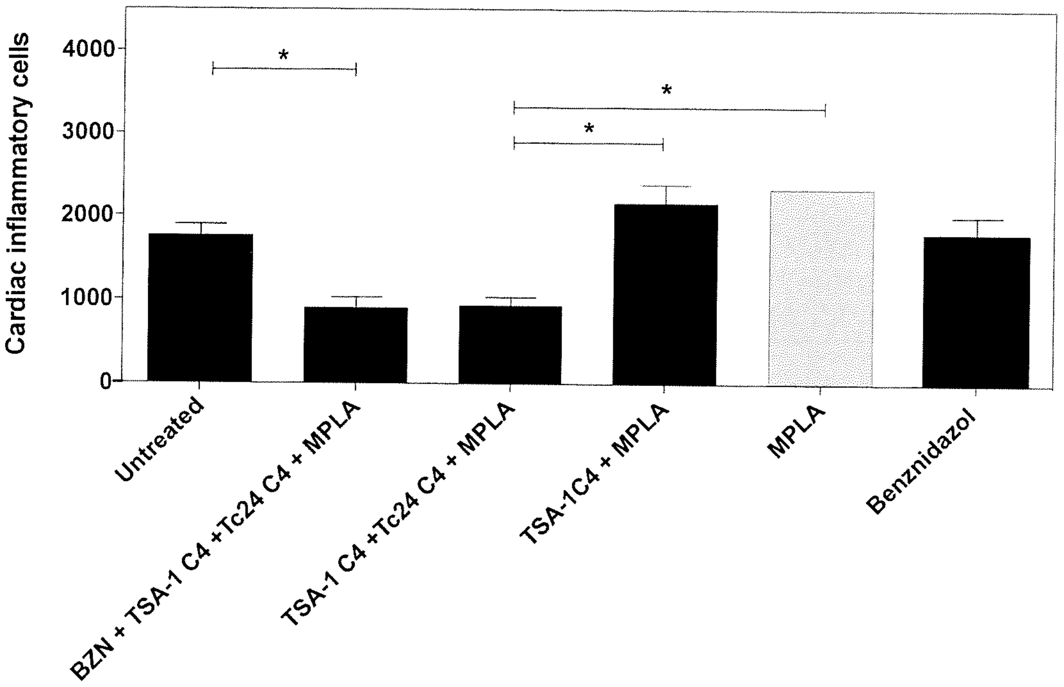
FIG. 12. Inflammatory cells in cardiac tissue. H1 *Trypanosoma cruzi* infected-mice treated with TSA-1-C4 alone or with Tc24-C4 and in a combination with or without BZN treatment were euthanized at 50 dpi and sections of cardiac tissue were stained with H&E. Four or five pictures were taken with an optical microscope and analyzed by Multispec 2.0 software. Treated mice received Tc24 and TSA-1-C4 20 μg each and given orally 25 mg/kg BZN per day for 20 days. Histograms represent the mean and standard bars the error of the mean. (*) Statistically significant differences were observed with a P value <0.05.

The results are shown in FIGS. 11A and B and FIG. 12. Briefly, H1 *Trypanosoma cruzi*-infected mice were treated with Tc24-C4 and TSA-1-C4, 20 μg each and given orally 25 mg/kg BZN per day for 20 days. Kinetic parasitemia was recorded each 3 days during the acute infection (FIG. 11A), and the area under the curve (AUC) was graphed (FIG. 11B). The results showed significantly lower levels of parasites in the blood of mice who received TSA-1-C4 or Tc24-C4 and TSA-1-C4 together, compared to untreated controls.

Inflammatory cells in cardiac tissue were quantitated and the data is presented in FIG. 12. Briefly, H1 *Trypanosoma cruzi* infected-mice were treated with TSA-1-C4 alone or with Tc24-C4 and in a combination with or without BZN treatment, euthanized at 50 dpi and sections of cardiac tissue were stained with H&E. The results showed that mice immunized with Tc24-C4 and TSA-1-C4 together had significantly lower levels of inflammatory cells, compared to untreated mice.

While the invention has been described in terms of its preferred embodiments, those skilled in the art will recognize that the invention can be practiced with modification within the spirit and scope of the appended claims. Accordingly, the present invention should not be limited to the embodiments as described above, but should further include all modifications and equivalents thereof within the spirit and scope of the description provided herein.

What is claimed is:

1. A recombinant protein comprising SEQ ID NO: 1, wherein X1, X2, X3 and X4 are Ser.

2. The recombinant protein of claim 1, further comprising a C-terminal histidine tag.

3. A composition comprising the recombinant protein according to claim 1.

4. The composition of claim 3, further comprising the recombinant protein encoded by SEQ ID NO: 7.

5. The composition of claim 3, further comprising an adjuvant.

6. The composition of claim 5, wherein the adjuvant is monophosphoryl lipid A (MPLA).

7. A method of treating at least one symptom of a *Trypanosoma cruzi* infection in a subject in need thereof, comprising administering to the subject a therapeutically effective amount of the recombinant protein of claim 1.

8. The method of claim 7, wherein the subject is a human, horse, cow, dog, cat, goat, sheep, or pig.

9. The method of claim 7, further comprising a step of diagnosing the *T. cruzi* infection.

10. The method of claim 7, wherein the at least one symptom of a *Trypanosoma cruzi* infection is a symptom of acute infection or a symptom of chronic infection.

11. The method of claim 10, wherein the symptom of acute infection is one or more of: swelling at the infection site, fever, fatigue, rash, body aches, eyelid swelling, headache, loss of appetite, swollen glands and enlargement of the liver or spleen.

12. The method of claim 10, wherein the symptom of chronic infection is one or more of: irregular heartbeat, congestive heart failure, sudden cardiac arrest, difficulty swallowing due to an enlarged esophagus, abdominal pain due to enlarged colon or constipation due to enlarged colon.

13. The method of claim 7, further comprising administering benznidazole to the subject.

14. A method of decreasing the number of inflammatory cells in heart tissue of a subject infected with *T. cruzi*, comprising administering to the subject a therapeutically effective amount of: the recombinant protein of claim 1.

* * * * *